United States Patent
Wang

(10) Patent No.: US 11,970,517 B2
(45) Date of Patent: Apr. 30, 2024

(54) COMPOSITIONS AND METHODS FOR DISSOLVING PROTEIN AGGREGATES

(71) Applicant: REJUKON BIOPHARM INC., Shanghai (CN)

(72) Inventor: Chenchen Wang, Shanghai (CN)

(73) Assignee: REJUKON BIOPHARM INC., Shanghai (CN)

( * ) Notice: Subject to any disclaimer, the term of this patent is extended or adjusted under 35 U.S.C. 154(b) by 0 days.

(21) Appl. No.: 17/887,501

(22) Filed: Aug. 14, 2022

(65) Prior Publication Data

US 2023/0142083 A1 May 11, 2023

Related U.S. Application Data

(63) Continuation of application No. PCT/CN2021/111683, filed on Aug. 10, 2021.

(30) Foreign Application Priority Data

Aug. 10, 2020 (CN) .......................... 202010796060.4

(51) Int. Cl.
| | |
|---|---|
| C07K 14/00 | (2006.01) |
| A61K 48/00 | (2006.01) |
| A61P 25/28 | (2006.01) |
| C12N 15/86 | (2006.01) |
| A61K 38/00 | (2006.01) |

(52) U.S. Cl.
CPC ............ *C07K 14/001* (2013.01); *A61P 25/28* (2018.01); *C12N 15/86* (2013.01); *A61K 38/00* (2013.01); *A61K 48/00* (2013.01); *C12N 2750/14143* (2013.01)

(58) Field of Classification Search
CPC ....... C07K 14/001; A61P 25/28; C12N 15/86; A61K 48/00
See application file for complete search history.

(56) References Cited

U.S. PATENT DOCUMENTS

| | | | |
|---|---|---|---|
| 2015/0166567 A1 | 6/2015 | Chambers et al. | |
| 2018/0250356 A1 | 9/2018 | Twiss et al. | |

FOREIGN PATENT DOCUMENTS

| | | |
|---|---|---|
| CN | 105473153 A | 4/2016 |
| CN | 107652357 A | 2/2018 |
| CN | 109223755 A | 1/2019 |
| CN | 109414482 A | 3/2019 |
| CN | 110241204 A | 9/2019 |
| CN | 110997693 A | 4/2020 |
| CN | 111051331 A | 4/2020 |
| CN | 111886247 A | 11/2020 |
| CN | 114796451 A | 7/2022 |
| JP | 2016523236 A | 8/2016 |
| WO | 9639834 A1 | 12/1996 |
| WO | 2002064619 A2 | 8/2002 |
| WO | 2010037135 A2 | 4/2010 |
| WO | 2012123419 A1 | 9/2012 |
| WO | 2016014908 A1 | 1/2016 |
| WO | 2019134981 A1 | 7/2019 |
| WO | 2017177178 A1 | 4/2020 |
| WO | 2021207636 A2 | 10/2021 |

OTHER PUBLICATIONS

Ju Gao et al., TDP-43 inhibitory peptide alleviates neurodegeneration and memory loss in an APP transgenic mouse model for Alzheimer's disease, Biochimica et Biophysica Acta (BBA)—Molecular Basis of Disease, Oct. 31, 2019, vol. 1866, No. 1, pp. 1-27.
Yanlin Chen et al., The protective effects of dulaglutide on AD-like neurodegenerative changes, Tianjin Medical, Jul. 15, 2018, vol. 46, No. 7, pp. 673-677.
First Office Action of Chinese application No. 202010796060.4, dated Sep. 22, 2022.
Search report of Chinese application No. 202010796060.4, dated Sep. 22, 2022.
Nanoscopic Insights of Amphiphilic Peptide against the Oligomer Assembly Process to Treat Huntington's Disease, He, R. Y. et al., Advanced Science (Dec. 9, 2019), vol. 7, abstract, supplementary Table 1, p. 10.
Peptide Aggregation in Neurodegenerative Disease Annual Review of Biomedical Engineering, Murphy, R. M. et al., (Dec. 31, 2002), vol. 4, pp. 155-174.
Inhibition of amyloid fibril formation of β-amyloid peptides via the amphiphilic surfactants, Wang, S. S. S. et al., Biochimica et Biophysica Acta (BBA)—Molecular Basis of Disease (Jun. 16, 2005), No. 3, vol. 1741, pp. 307-313.
Sulfated and sulfonated polymers are able to solubilize efficiently the protein aggregates of different nature, Semenyuk, P. I. et al., Archives of Biochemisitry and Biophysics (Jan. 3, 2015), vol. 567, pp. 22-29.
Inhibition of Polyglutamine Protein Aggregation and Cell Death by Novel Peptides Identified by Phage Display Screening, Nagai, Y. et al., The Journal of Biological Chemistry (Apr. 7, 2000), No. 14, vol. 275, pp. 10437-10442.
International search report of PCT application No. PCT/CN2021/111683, dated Nov. 11, 2021.
Office Action of the corresponding Japanese application No. 2023-509613, dated Sep. 20, 2023.
Mishra A. et al. "Structure-Based Design of Small Peptide Ligands to Inhibit Early-Stage Protein Aggregation Nucleation" J. Chem. Inf. Model. (2020) 60(6): 3304-3314.
He et al. "Nanoscopic Insights of Amphiphilic Peptide against the Oligomer Assembly Process to Treat Huntington's Disease" Adv. Sci. (2020) 7: 1901165.
Examination Report No. 1 of the corresponding Australian application No. 2021325233, dated Apr. 5, 2023.

(Continued)

*Primary Examiner* — Olga N Chernyshev
(74) *Attorney, Agent, or Firm* — Jun He Law Offices P.C.; James J. Zhu

(57) ABSTRACT

The present disclosure provides a polypeptide capable of dissolving protein aggregates. Also provided is a method of treating a neurodegeneration disease using the polypeptide.

15 Claims, 11 Drawing Sheets

Specification includes a Sequence Listing.

(56) References Cited

OTHER PUBLICATIONS

Rui Liu et al.: "Reducing TDP-43 aggregation does not prevent its cytotoxicity", Acta Neuropathologica Communication, Biomed Central Ltd, London, UK, vol. 1, No. 1, Aug. 9, 2013 (Aug. 9, 2013), p. 49, XP021162775, ISSN: 2051-5960, DOI: 10.1186/2051-5960-1-49, the whole document.

Prasad Archana et al.: "Molecular Mechanisms of TDP-43 Misfolding and Pathology in Amyotrophic Lateral Sclerosis", Frontiers in Molecular Neuroscience, vol. 12, Feb. 14, 2019 (Feb. 14, 2019), XP055791761, DOI: 10.3389/fnmol. 2019.00025, the whole document.

Abrakhi Sanae El Al: "Nanoscale Analysis Reveals the Maturation of Neurodegeneration-Associated Protein Aggregates: Grown in mRNA Granules then Released by Stress Granule Proteins", ACS NANO, vol. 11, No. 7, Jul. 5, 2017 (Jul. 5, 2017), pp. 7189-7200, XP093107259, US ISSN: 1936-0851, DOI: 10.1021/acsnano. 7b03071, the whole document.

The Extended European Search Report of the corresponding European application No. 21855506.8 issued on Dec. 20, 2023.

RJK001 (SEQ ID NO:1)
TEPQEESEEEVEEPEERQQTPEVVPDDSGTFYDQTVSNDLE

RJK002 (SEQ ID NO:2)
TDPQDDSDDDVDDPDDRQQTPDVVPDDSGTFYDQTVSNDLD

RJK003 (SEQ ID NO:3)
TKPQKKSKKKVKKPKKRQQTPKVVPDDSGTFYDQTVSNDLK

RJK004 (SEQ ID NO:4)
TRPQRRSRRRVRRPRRRQQTPRVVPDDSGTFYDQTVSNDLR

RJK005 (SEQ ID NO:5)
TQPQQQSQQQVQQPQQRQQTPQVVPDDSGTFYDQTVSNDLQ

RJK006 (SEQ ID NO:6)
TEPQEESEEEVEEPEERQQTPEVVPDDSGTFY

RJK007 (SEQ ID NO:7)
TEPQEESEEEVEEPEERQQTPEVVPDD

RJG001 (SEQ ID NO:8)
ELDEESEDEVEEEQEDRQPSPEPVQENANSAYYDAHPVTNGIE

RJG002 (SEQ ID NO:9)
KEEVDEDRDVDESSPQDSPPSKASPAQDGRPPQTAAREATSIPGFPAEGAIPLPV

RJG003 (SEQ ID NO:10)
EGEVAEEPNSRPQEKSEQDLE

FIG. 1

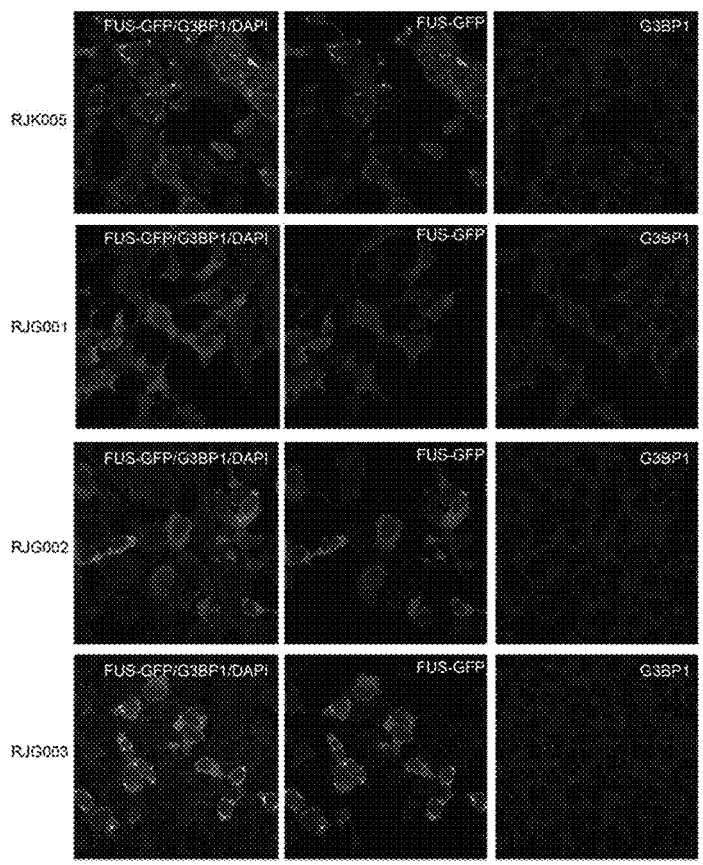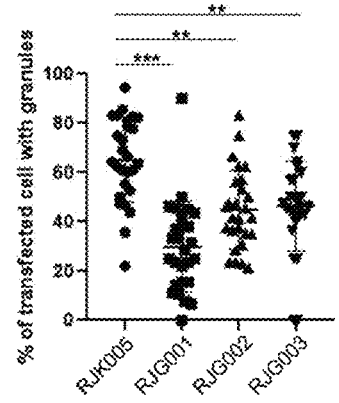
FIG. 12

| Abbreviation | 1 letter abbreviation | Amino acid name |
|---|---|---|
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |
| Xaa | X | Any amino acid |

FIG. 13

COMPOSITIONS AND METHODS FOR DISSOLVING PROTEIN AGGREGATES

CROSS-REFERENCE TO RELATED APPLICATIONS

This application claims priority to Chinese patent application no. 202010796060.4, filed Aug. 10, 2020, the disclosure of which is incorporated herein by reference in their entirety.

SEQUENCE LISTING

The sequence listing that is contained in the file named "081734-8001US01-sequence list", which is 39,023 bytes and was created on Oct. 30, 2022, is filed herewith by electronic submission and is incorporated by reference herein.

FIELD OF THE INVENTION

The present invention generally relates to neurobiology and neurodegenerative disease. In particular, the present invention relates to compositions and methods for dissolving pathogenic protein aggregates.

BACKGROUND OF THE INVENTION

Protein aggregation is a common feature of many neurodegenerative diseases, such as amyotrophic lateral sclerosis (ALS), Alzheimer's disease, Parkinson's disease and Huntington's disease. The protein aggregates in neurons, such as FUS in ALS, amyloid-beta in Alzheimer's disease, alpha-synuclein in Parkinson's disease and huntingtin in Huntington's disease, appear to be toxic, causing injury or death to neurons. In general, the degree of aggregation is proportional to the severity of the neurodegenerative disease.

While the causes of protein aggregation in neurons are not completely understood, it appears that the aggregation-prone proteins are often supersaturated in the cells, i.e., the cellular concentration of the protein exceeds the thermodynamic solubility but remain in a metastable liquid-like state by buffering via heterotypic interactions. Disturbance of metastable form of supersaturation would cause the loss of protein solubility and lead to protein aggregation.

Several attempts have been made to develop therapeutics for neurodegenerative diseases by inhibiting protein aggregation or dissolving pathogenic protein aggregates. For example, compounds capable of inhibiting protein aggregation have been disclosed in U.S. Pat. Nos. 10,435,373, 9,738,635, 10,889,584, 9,284,309, 9,527,852, and 9,7901,88. U.S. Pat. No. 9,845,327 discloses inhibiting protein aggregation by promoting lysosomal activation. However, because there is still no known way to reverse the progressive degeneration of neurons, neurodegenerative diseases are considered as incurable. Therefore, there are needs to develop new compositions and methods to inhibit protein aggregation or dissolve protein aggregates in neurons.

BRIEF SUMMARY OF THE INVENTION

In one aspect, the present disclosure provides a polypeptide capable of dissolving protein aggregates. In some embodiments, the polypeptide comprises a hydrophilic segment and a hydrophobic segment, said hydrophilic segment having a length of 10-20 amino acid residues among which at least 50% are Asp, Glu, Lys, or Arg, said hydrophobic segment having a length of 10-20 amino acid residues among which at least 50% are Tyr, Phe, Trp, Leu, Ile, Val, Met, Pro, Ala, or Cys, wherein the hydrophilic segment is at the N-terminus and the hydrophobic segment is at the C-terminus, or vice versa, and wherein the polypeptide has a length of 20-60 amino acid residues.

In some embodiments, the hydrophilic segment has a sequence of selected from the group consisting of $TX_1PQX_1X_1SX_1X_1X_1VX_1X_1PX_1X_1X_1$ (SEQ ID NO: 11), $X_1LX_1X_1X_1SX_1X_1X_1VX_1X_1X_1QX_1X_1X_1$ (SEQ ID NO: 12), $X_1X_1X_1VX_1X_1X_1X_1X_1VX_1X_1$ (SEQ ID NO: 13), and $X_1X_1SX_1VQX_1LX_1$ (SEQ ID NO: 14), wherein each $X_1$ is respectively Asp, Glu, Lys or Arg.

In some embodiments, the hydrophilic segment has a sequence selected from the group consisting of TEPQEESEEEVEEPEER (SEQ ID NO: 15), TDPQDDSDDDVDDPDDR (SEQ ID NO: 16), TKPQKKSKKKVKKPKKR (SEQ ID NO: 17), TRPQRRSRRRVRRPRRR (SEQ ID NO: 18), ELDEESEDEVEEEQEDR (SEQ ID NO: 19), KEEVDEDRDVDE (SEQ ID NO: 20), and EKSEQDLE (SEQ ID NO: 21), or a sequence having at least 90% identity thereto, or a sequence having 1, 2, 3, 4, or 5 amino acid residue difference therefrom.

In some embodiments, the hydrophilic segment the hydrophobic segment has a sequence selected from: TFYDQTVSNDL (SEQ ID NO: 22), ANSAYYDAHPVTNGI (SEQ ID NO: 23), PPQTAAREATSIPGFPAEGAIPLPV (SEQ ID NO: 24), and EGEVAEEPNSRP (SEQ ID NO: 25), or a sequence having at least 90% identity thereto, or a sequence having 1, 2, 3, 4, or 5 amino acid residue difference therefrom.

In some embodiments, the polypeptide has a sequence selected from the group consisting of

```
                                          (SEQ ID NO: 1)
TEPQEESEEEVEEPEERQQTPEVVPDDSGTFYDQTVSNDLE, (SEQ ID NO: 2)
TDPQDDSDDDVDDPDDRQQTPDVVPDDSGTFYDQTVSNDLD, (SEQ ID NO: 3)
TKPQKKSKKKVKKPKKRQQTPKVVPDDSGTFYDQTVSNDLK, (SEQ ID NO: 4)
TRPQRRSRRRVRRPRRRQQTPRVVPDDSGTFYDQTVSNDLR, (SEQ ID NO: 8)
ELDEESEDEVEEEQEDRQPSPEPVQENANSAYYDAHPVINGIE, (SEQ ID NO: 9)
KEEVDEDRDVDESSPQDSPPSKASPAQDGRPPQTAAREATSIPGFPAEG
AIPLPV,
and (SEQ ID NO: 10)
EGEVAEEPNSRPQEKSEQDLE,
``` or a sequence having at least 90% identity thereto, or a sequence having 1, 2, 3, 4, or 5 amino acid residue difference therefrom.

In some embodiments, the protein aggregate is FUS aggregate, TDP43 aggregate, TIA1 aggregate, C9orf72 aggregate or a combination thereof. In some embodiments, the protein aggregate is beta-amyloid aggregate, alpha-synuclein aggregate, or huntingtin aggregate.

In another aspect, the present disclosure provides a polynucleotide encoding the polypeptide described herein. In some embodiments, the polynucleotide is a DNA or an RNA.

In another aspect, the present disclosure provides a vector comprising the polynucleotide disclosed herein. In some embodiments, the vector is a virus vector. In some embodiments, the vector is an AAV vector.

In another aspect, the present disclosure provides a recombinant virus comprising the polynucleotide disclosed herein. In some embodiments, the recombinant virus is an AAV.

In another aspect, the present disclosure provides a host cell comprising the polynucleotide disclosed herein.

In another aspect, the present disclosure provides a pharmaceutical composition. In some embodiments, the pharmaceutical composition comprises (1) the polypeptide disclosed herein, the polynucleotide disclosed herein, the vector disclosed herein, or the recombinant virus disclosed herein. In some embodiments, the pharmaceutical composition comprises a pharmaceutically acceptable carrier.

In another aspect, the present disclosure provides a method for dissolving protein aggregates in a cell. In some embodiments, the method comprises introducing to the cell the polypeptide disclosed herein. In some embodiments, the cell is a neuronal cell. In some embodiments, the protein aggregate is FUS protein aggregate, and the cell is a motor neuron. In some embodiments, the cell is in vitro or in vivo.

In another aspect, the present disclosure provides a method for treating a neurodegeneration disease in a subject in need thereof. In some embodiments, the method comprises administering to the subject a therapeutic effective amount of the pharmaceutical composition disclosed herein. In some embodiments, the neurodegeneration disease is selected from frontotemporal dementia, amyotrophic lateral sclerosis, cortical basal ganglia degeneration, Lewy body dementia, Huntington's disease, Lewy body disease, motor neuron disease, frontotemporal degeneration, hippocampal sclerosis, inclusion body myopathy, inclusion body Myositis, Parkinson's disease, argyrophilic granular disease, Alzheimer's disease, Parsons/dementia complex in the Kii Peninsula, progressive supranuclear palsy, and Pick's disease. In some embodiments, the pharmaceutical composition is administered to the central nervous system. In some embodiments, the pharmaceutical composition is administered via spinal cord injection, intrathecal injection, intracerebroventricular injection, intracerebral injection, or intrahippocampal injection.

In yet another aspect, the present disclosure provides a method of identifying a polypeptide capable of dissolving a protein aggregate. In some embodiments, the method comprises: identifying a protein having a disordered region, wherein the disordered region comprises (a) at least two amino acid residues of Gln, (b) at least 6 hydrophilic amino acid residues selected from Arg, Lys, Asp, Glu and Asn, and (c) at least 6 hydrophobic amino acid residues selected from Phe, Cys, Leu, Val and Ile; generating a polypeptide consisting essentially of the disordered region; contacting the polypeptide with a protein aggregate; and determining that the polypeptide dissolves the protein aggregate. In some embodiments, the polypeptide has a length of 20-60 amino acid residues. In some embodiments, the polypeptide comprises a hydrophilic segment at the N-terminus and a hydrophobic segment at the C-terminus, or vice versa.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description of specific embodiments presented herein.

FIG. 1 shows the sequences of the exemplary polypeptides of the present disclosure.

FIG. 12 shows the effect of RJG001~RJG003 polypeptide on the FUS protein aggregates in the SH-SY5Y cell mode. Polypeptides RJG001~RJG003 and control polypeptide RJK005 were transfected into the SH-SY5Y cell model overexpressing FUS-mCherry after heat stimulation. The staining of G3BP1 represents the stress granule. RJG001~RJG003 polypeptides had a significant dissolution effect on the ALS pathogenic FUS aggregates, but the control polypeptides RJK005 had no effect on the pathogenic FUS protein aggregates.

FIG. 13 shows the amino acid codes.

DETAILED DESCRIPTION OF THE INVENTION

Figure 2:
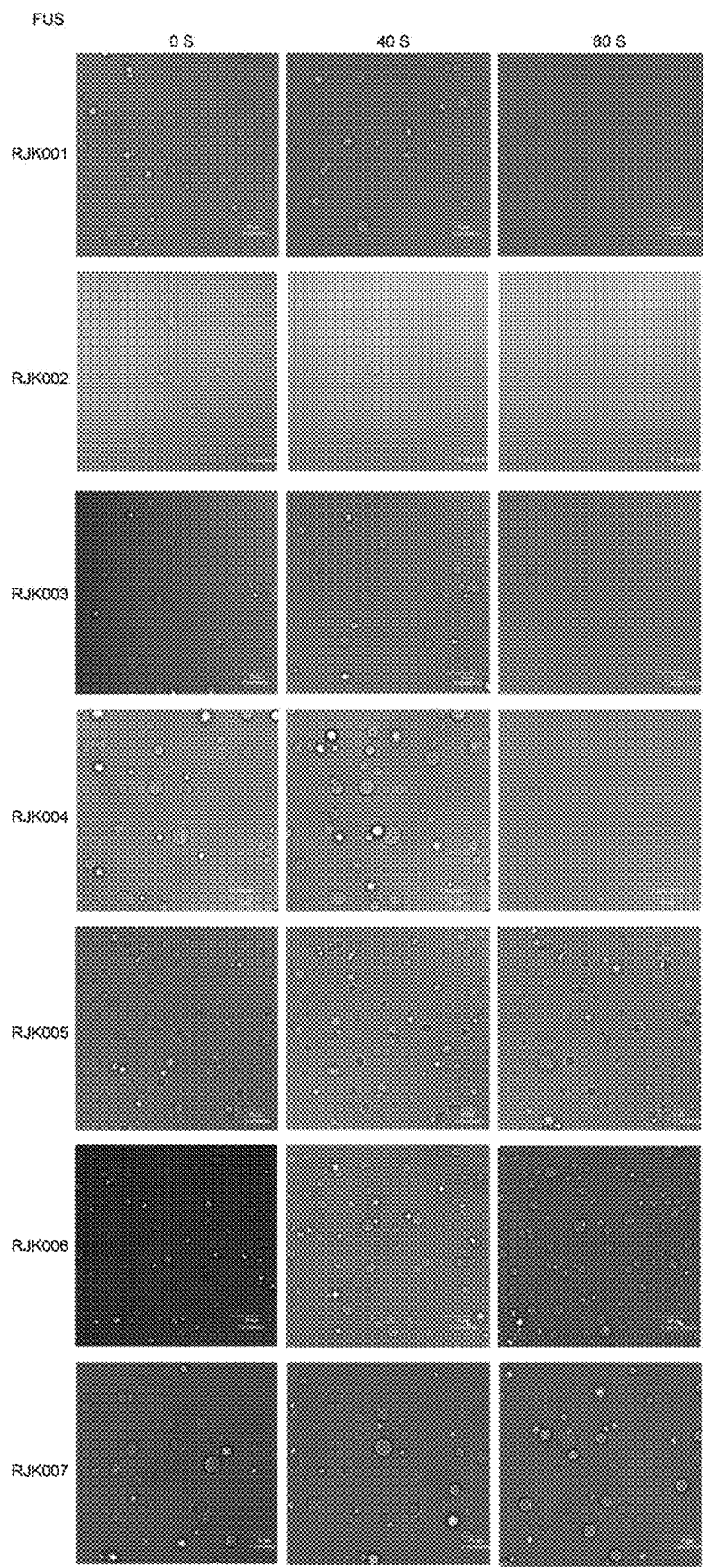
FIG. 2 shows that polypeptides RJK001~RJK004 dissolved FUS protein aggregates in vitro. The prokaryotic expressed and purified FUS protein (pH7.5, 10 uM FUS) was induced to form phase separated droplets in vitro. Polypeptides RJK001~RJK007 (30 uM) were added dropwise to the FUS droplets. The observation was performed continuously through a confocal laser microscope. The left image is the microscopic image just after adding the polypeptides. The middle image is the microscopic image after the polypeptides were added for 40 seconds. The right image is the microscopic image after the polypeptides were added for 80 seconds.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definition

It is to be understood that both the foregoing general description and the following detailed description are exemplary and explanatory only and are not restrictive of the invention as claimed. In this application, the use of the singular includes the plural unless specifically stated otherwise. In this disclosure, the term "or" is used to mean "and/or" unless explicitly indicated to refer to alternatives only or the alternatives are mutually exclusive. As used herein "another" may mean at least a second or more. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

As used herein, the term "administering" means providing a pharmaceutical agent or composition to a subject, and includes, but is not limited to, administering by a medical professional and self-administering.

The term "amino acid" as used herein refers to an organic compound containing amine ($-NH_2$) and carboxyl ($-COOH$) functional groups, along with a side chain specific to each amino acid. The names of amino acids are also represented as standard single letter or three-letter codes in the present disclosure.

A "cell", as used herein, can be prokaryotic or eukaryotic. A prokaryotic cell includes, for example, bacteria. A eukaryotic cell includes, for example, a fungus, a plant cell, and an animal cell. Preferably, the cell described herein is an animal cell. The types of an animal cell (e.g., a mammalian cell or a human cell) includes, for example, a cell from a nervous system or organ, e.g., a neuron, a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte); a cell from a respiratory system or organ, e.g., a pneumocyte (a type I pneumocyte and a type II pneumocyte), a clara cell, a goblet cell, an alveolar macrophage; a cell from circular system or organ, e.g., myocardiocyte and pericyte; a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., a myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula *densa* cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A mammalian cell can be a rodent cell, e.g., a mouse, rat, hamster cell. A mammalian cell can be a lagomorpha cell, e.g., a rabbit cell. A mammalian cell can also be a primate cell, e.g., a human cell As used herein, the term "effective amount" or "therapeutically effective amount" means the amount of agent that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount sufficient to reduce or eliminate a symptom of a disease. In another embodiment, a therapeutically effective amount is an amount sufficient to overcome the disease itself.

The term "host cell" means a cell that has been transformed, or is capable of being transformed, with a nucleic acid sequence and thereby expresses a protein of interest. The term includes the progeny of the parent cell, whether or not the progeny is identical in morphology or in genetic make-up to the original parent cell, so long as the gene of interest is present.

The term "nucleic acid" or "polynucleotide" as used herein refers to deoxyribonucleic acids (DNA) or ribonucleic acids (RNA) and polymers thereof in either single- or double-stranded form. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al., *J. Mol. Biol.*, 215:403-410 (1990); Stephen F. et al., *Nucleic Acids Res.*, 25:3389-3402 (1997)), ClustalW2 (available on the website of European Bioinformatics Institute, see also, Higgins D. G. et al., *Methods in Enzymology*, 266:383-402 (1996); Larkin M. A. et al., Bioinformatics (Oxford, England), 23(21): 2947-8 (2007)), and ALIGN or Megalign (DNASTAR) software. A person skilled in the art may use the default parameters provided by the tool or may customize the parameters as appropriate for the alignment, such as for example, by selecting a suitable algorithm.

The term "polypeptide" or "protein" means a string of at least two amino acids linked to one another by peptide bonds. Polypeptides and proteins may include moieties in addition to amino acids (e.g., may be glycosylated) and/or may be otherwise processed or modified. Those of ordinary skill in the art will appreciate that a "polypeptide" or "protein" can be a complete polypeptide chain as produced by a cell (with or without a signal sequence) or can be a functional portion thereof. Those of ordinary skill will further appreciate that a polypeptide or protein can sometimes include more than one polypeptide chain, for example linked by one or more disulfide bonds or associated by other means. The term also includes amino acid polymers in which one or more amino acids are chemical analogs of a corresponding naturally occurring amino acid and polymers.

The phrase "pharmaceutically acceptable carrier" as used herein means a pharmaceutically acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "protein aggregate" used herein refers the aggregation of a protein which appears either intra or extracellularly. In some embodiments, the protein is an intrinsically disordered protein or a mis-folded protein. In some embodiments, the aggregation occurs when the concentration of the protein exceeds the solubility of the protein. In some embodiments, the concentration of the protein exceeds the thermodynamic solubility, but the protein remains in a metastable liquid-like state by buffering via heterotypic interactions. Disturbance of metastable form of the protein would cause the loss of protein solubility and lead to protein aggregation.

The term "recombinant" when used with reference to a polypeptide (e.g., antibody, antigen) or a polynucleotide, refers to a polypeptide or polynucleotide that is produced by a recombinant method. A "recombinant polypeptide" includes any polypeptide expressed from a recombinant polynucleotide. A "recombinant polynucleotide" includes any polynucleotide which has been modified by the introduction of at least one exogenous (i.e., foreign, and typically heterologous) nucleotide or the alteration of at least one native nucleotide component of the polynucleotide and need not include all of the coding sequence or the regulatory elements naturally associated with the coding sequence. A "recombinant vector" refers to a non-naturally occurring vector, including, e.g., a vector comprising a recombinant polynucleotide sequence.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Compositions for Dissolving Protein Aggregates

Protein aggregation is a biological phenomenon in which intrinsically disordered proteins or mis-folded proteins aggregate (i.e., accumulate and clump together) either intra- or extracellularly. Protein structures are stabilized by non-covalent interactions and disulfide bonds between two cysteine residues. The non-covalent interactions include ionic interactions and weak van der Waals interactions. Ionic interactions form between an anion and a cation and form salt bridges that help stabilize the protein. Van der Waals interactions include nonpolar interactions and polar interactions (i.e., hydrogen bonds, dipole-dipole bond). These play an important role in a protein's secondary structure, such as forming an alpha helix or a beta sheet, and tertiary structure. Interactions between amino acid residues in a specific protein are very important in that protein's final structure.

When there are changes in the non-covalent interactions, as may happen with a change in the amino acid sequence, the protein is susceptible to misfolding or unfolding. In these cases, if the cell does not assist the protein in re-folding, or degrade the unfolded protein, the unfolded/misfolded protein may aggregate, in which the exposed hydrophobic portions of the protein may interact with the exposed hydrophobic patches of other proteins. There are three main types of protein aggregates that may form: amorphous aggregates, oligomers, and amyloid fibrils. Mis-folded protein aggregates are often correlated with diseases. For example, protein aggregates have been implicated in a wide variety of neurodegenerative diseases, including ALS, Alzheimer's disease, Parkinson's disease, Huntington's disease and prion disease.

The present disclosure is based on the surprising discovery that fragments of certain naturally occurring proteins, such as G3BP1, are capable of dissolving protein aggregates. In particular, such fragments are generally amphipathic—the fragments comprise a hydrophilic segment at one end and a hydrophobic segment at the other. The inventor also surprisingly found that certain variants of the fragments in which the hydrophilic amino acid residues are replaced with other hydrophilic amino acid residues keep the property of dissolving protein aggregates.

Therefore, the present disclosure in one aspect provides a polypeptide capable of dissolving protein aggregates. In some embodiments, the polypeptide comprises a hydrophilic segment and a hydrophobic segment, said hydrophilic segment having a length of 10-20 amino acid residues among which at least 50% are Asp, Glu, Lys, or Arg, said hydrophobic segment having a length of 10-20 amino acid residues among which at least 50% are Tyr, Phe, Trp, Leu, Ile, Val, Met, Pro, Ala, or Cys, wherein the hydrophilic segment is at the N-terminus and the hydrophobic segment is at the C-terminus, or vice versa, and wherein the polypeptide has a length of 20-60 amino acid residues.

In some embodiments, the hydrophilic segment has a sequence of selected from the group consisting of TX$_1$PQX$_1$X$_1$SX$_1$X$_1$X$_1$VX$_1$X$_1$PX$_1$X$_1$X$_1$ (SEQ ID NO: 11), X$_1$LX$_1$X$_1$X$_1$SX$_1$X$_1$X$_1$VX$_1$X$_1$X$_1$QX$_1$X$_1$X$_1$ (SEQ ID NO: 12), X$_1$X$_1$X$_1$VX$_1$X$_1$X$_1$X$_1$X$_1$VX$_1$X$_1$ (SEQ ID NO: 13), and X$_1$X$_1$SX$_1$VQX$_1$LX$_1$ (SEQ ID NO: 14), wherein each X$_1$ is respectively Asp, Glu, Lys or Arg.

In some embodiments, the hydrophilic segment has a sequence selected from the group consisting of TEPQEESEEEVEEPEER (SEQ ID NO: 15), TDPQDDSDDDVDDPDDR (SEQ ID NO: 16), TKPQKKSKKKVKKPKKR (SEQ ID NO: 17), TRPQRRSRRRVRRPRRR (SEQ ID NO: 18), ELDEESEDEVEEEQEDR (SEQ ID NO: 19), KEEVDEDRDVDE (SEQ ID NO: 20), and EKSEQDLE (SEQ ID NO: 21), or a sequence having at least 90% identity thereto, or a sequence having 1, 2, 3, 4, or 5 amino acid residue difference therefrom.

In some embodiments, the hydrophilic segment the hydrophobic segment has a sequence selected from: TFYDQTVSNDL (SEQ ID NO: 22), ANSAYYDAHPVTNGI (SEQ ID NO: 23), PPQTAAREATSIPGFPAEGAIPLPV (SEQ ID NO: 24), and EGEVAEEPNSRP (SEQ ID NO: 25), or a sequence having at least 90% identity thereto, or a sequence having 1, 2, 3, 4, or 5 amino acid residue difference therefrom.

The polypeptide of claim 1, having a sequence selected from the group consisting of

```
                                     (SEQ ID NO: 1)
TEPQEESEEEVEEPEERQQTPEVVPDDSGTFYDQTVSNDLE, (SEQ ID NO: 2)
TDPQDDSDDDVDDPDDRQQTPDVVPDDSGTFYDQTVSNDLD, (SEQ ID NO: 3)
TKPQKKSKKKVKKPKKRQQTPKVVPDDSGTFYDQTVSNDLK, (SEQ ID NO: 4)
TRPQRRSRRRVRRPRRRQQTPRVVPDDSGTFYDQTVSNDLR, (SEQ ID NO: 8)
ELDEESEDEVEEEQEDRQPSPEPVQENANSAYYDAHPVINGIE, (SEQ ID NO: 9)
KEEVDEDRDVDESSPQDSPPSKASPAQDGRPPQTAAREATSIPGFPAEG
AIPLPV,
and (SEQ ID NO: 10)
EGEVAEEPNSRPQEKSEQDLE,
``` or a sequence having at least 90% identity thereto, or a sequence having 1, 2, 3, 4, or 5 amino acid residue difference therefrom.

In some embodiments, the protein aggregate is pathogenic in neurodegenerative diseases. In some embodiments, the protein aggregate is FUS aggregate, TDP43 aggregate, TIA1 aggregate, C9orf72 aggregate or a combination thereof. In some embodiments, the protein aggregate is beta-amyloid aggregate, alpha-synuclein aggregate, or huntingtin aggregate.

In another aspect, the present disclosure provides a polynucleotide encoding the polypeptide described herein. In some embodiments, the polynucleotide is a DNA or an RNA. In some embodiments, the polynucleotide is single strand DNA or double strand DNA.

In another aspect, the present disclosure provides a vector comprising the polynucleotide disclosed herein. Typically, the vector further comprises additional elements that facilitate the expression of the polypeptide, such as promoter, enhancer, polyA region, etc. In some embodiments, the vector is a virus vector. In some embodiments, the vector is an adeno-associated virus (AAV) vector. In some embodiments, the AAV vector further comprises an ITR sequence.

In another aspect, the present disclosure provides a recombinant virus comprising the polynucleotide disclosed herein. In some embodiments, the recombinant virus is an AAV. In some embodiments, the AAV has a serotype selected from AAV1, AAV2, AAV3, AAV5, AAV6, AAV7, AAV8, AAVrh8, AAV9, AAV10, AAVrh10, AAV11 and AAV12.

In another aspect, the present disclosure provides a host cell comprising the polynucleotide disclosed herein. The host cell can be used to express the polypeptide disclosed herein or to generate the virus disclosed herein.

In another aspect, the present disclosure provides pharmaceutical compositions comprising the polypeptide, the polynucleotide, the vector, the recombinant virus, or the host cell disclosed herein. Such compositions comprise a prophylactically or therapeutically effective amount of the polypeptide, the polynucleotide, the vector, the recombinant virus, or the host cell, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical agents are described in "Remington's Pharmaceutical Sciences." Such compositions will contain a prophylactically or therapeutically effective amount of the polypeptide, the polynucleotide, the vector, the recombinant virus, or the host cell, together with a suitable amount of carrier so as to provide the form for proper administration to the patient. The formulation should suit the mode of administration, which can be intrathecal, intravenous, intraarterial, intrabuccal, intranasal, nebulized, bronchial inhalation, or delivered by mechanical ventilation. Where the composition is administered by injection, an ampoule of sterile water for injection or saline can be provided so that the ingredients may be mixed prior to administration.

The compositions of the present disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Methods of Identification

The present disclosure in another aspect provides a method for identifying a polypeptide capable of dissolving a protein aggregate. In some embodiments, the method comprises: identifying an intrinsically disordered protein having a disordered region, wherein the disordered region comprises (a) at least two amino acid residues of Gln, and/or (b) at least 6 hydrophilic amino acid residues selected from Arg, Lys, Asp, Glu and Asn, and/or (c) at least 6 hydrophobic amino acid residues selected from Phe, Cys, Leu, Val and Ile; generating a polypeptide consisting essentially of the disordered region; contacting the polypeptide with a protein aggregate; and determining that the polypeptide dissolves the protein aggregate. In some embodiments, the polypeptide has a length of 20-60 amino acid residues. In some embodiments, the polypeptide comprises a hydrophilic segment at the N-terminus and a hydrophobic segment at the C-terminus, or vice versa. In some embodiment, the protein is a naturally occurring intrinsically disordered protein.

In some embodiments, the disordered region comprises at least three, four, or five amino acid residues of Gln. In some embodiments, disordered region comprises at least 7, 8, 9 or 10 hydrophilic amino acid residues selected from Arg, Lys, Asp, Glu and Asn. In some embodiments, disordered region comprises at least 7, 8, 9 or 10 hydrophobic amino acid residues selected from Phe, Cys, Leu, Val and Ile.

Intrinsically disordered protein is a protein that lacks a fixed or ordered three-dimensional structure, typically in the absence of its interaction partner, such as other protein or RNA. Intrinsically disordered protein can be fully unstructured or partially structured. Naturally occurring intrinsically disordered proteins have been known in the art through literature or database. For example, DisProt database compiles intrinsically disordered proteins curated from literature (Hatos, A. et al., DisProt: Intrinsic protein disorder annotation in 2020, Nucleic Acids Research (2020) 48 (D1) 269-276). In some embodiments, the database (e.g., the DisProt database) is searched to identify an intrinsically disordered protein that contains a disordered region having the properties as described.

After the identification of the disordered region that meets the standard as described, a polypeptide that consists essentially of the disordered region can be generated recombinantly with the approaches known in the art. The polypeptide is then tested for its ability to dissolve protein aggregates, e.g., FUS aggregate, TDP43 aggregate, TIA1 aggregate, and C9orf72 aggregate. In some embodiment, the polypeptide is capable of dissolving at least 10%, 20%, 30%, 40%, 50%, 60%, 70%, 80%, 90% of the protein aggregate.

Variants of the polypeptide can be generated by replacing amino acid residues in the polypeptide such that the variant has a sequence of at least 90% identity to the polypeptide, or a sequence having 1, 2, 3, 4, or 5 amino acid residue difference from the polypeptide. The variants generated can then be tested for its ability to dissolve protein aggregates. In some embodiment, the variant has an improved capability of dissolving the protein aggregate compared to the polypeptide from which the variant is derived.

Methods of Use

In another aspect, the present disclosure provides a method of dissolving protein aggregates in a cell. In some embodiments, the method comprises introducing to the cell the polypeptide disclosed herein. In some embodiments, the cell is a neuron. In some embodiments, the protein aggregate is a FUS protein aggregate, a TDP-43 protein aggregate, a TIA1 protein aggregate, a beta-amyloid protein aggregate, an alpha-synuclein protein aggregate, or a huntingtin protein aggregate. In some embodiments, the polypeptide is introduced into the cell by contacting the cell with the polypeptide. In some embodiments, the polypeptide is introduced into the cell by introducing a polynucleotide encoding the polypeptide disclosed herein into the cell, thus allowing the cell to express the polypeptide. In some embodiments, the polynucleotide is introduced into the cell by transforming or transfecting the cell with a vector or virus comprising the polynucleotide.

In yet another aspect, the present disclosure provides a method of treating a disease or condition related to protein aggregation. In some embodiments, the disease or condition related to protein aggregation is a neurodegenerative disease. Neurodegenerative diseases result in the progressive loss of structure or function, and ultimately the cell death of neurons. Examples of neurodegenerative diseases include, without limitation, frontotemporal dementia, amyotrophic lateral sclerosis (ALS), cortical basal ganglia degeneration, Lewy body dementia, Huntington's disease, Lewy body disease, motor neuron disease, frontotemporal degeneration, hippocampal sclerosis, inclusion body myopathy, inclusion body Myositis, Parkinson's disease, argyrophilic granular disease, Alzheimer's disease, Parsons/dementia complex in the Kii Peninsula, progressive supranuclear palsy, and Pick's disease.

Amyotrophic lateral sclerosis (ALS) involves the degeneration of the upper motor neurons (UMNs) and lower motor neurons (LMNs) with the symptom of gradual progress of skeletal muscle weakness. Missense mutations in the gene encoding the antioxidant enzyme Cu/Zn superoxide dismutase 1 (SOD1) were discovered in a subset of patients with familial ALS. However, the pathogenic mechanism underlying SOD1 mutant toxicity has yet to be resolved. TDP-43 and FUS protein aggregates have also been implicated in some cases of the disease, and a mutation in chromosome 9 (C9orf72) is thought to be the most commonly known cause of sporadic ALS.

Alzheimer's disease (AD) is a chronic neurodegenerative disease that results in the loss of neurons and synapses in the cerebral cortex and certain subcortical structures, resulting in gross atrophy of the temporal lobe, parietal lobe, and parts of the frontal cortex and cingulate gyms. AD pathology is primarily characterized by the presence of senile plaques and neurofibrillary tangles. Plaques are made up of small peptides, typically 39-43 amino acids in length, called beta-amyloid (also written as A-beta or Aβ). Beta-amyloid is a fragment from a larger protein called amyloid precursor protein (APP), a transmembrane protein that penetrates through the neuron's membrane. APP appears to play roles in normal neuron growth, survival and post-injury repair. APP is cleaved into smaller fragments by enzymes such as gamma secretase and beta secretase. One of these fragments gives rise to fibrils of beta-amyloid which can self-assemble into the dense extracellular deposits known as senile plaques or amyloid plaques.

Parkinson's disease (PD) is the second most common neurodegenerative disorder. It typically manifests as bradykinesia, rigidity, resting tremor and posture instability. PD is primarily characterized by death of dopaminergic neurons in the substantia nigra, a region of the midbrain. The cause of this selective cell death is unknown. Notably, alpha-synuclein-ubiquitin complexes and aggregates are observed to accumulate in Lewy bodies within affected neurons. It is thought that defects in protein transport machinery and regulation, such as RAB1, may play a role in this disease mechanism. Impaired axonal transport of alpha-synuclein may also lead to its accumulation in Lewy bodies. Experiments have revealed reduced transport rates of both wildtype and two familial Parkinson's disease-associated mutant alpha-synucleins through axons of cultured neurons.

Huntington's disease (HD) is a rare autosomal dominant neurodegenerative disorder caused by mutations in the huntingtin gene (HTT). HD is characterized by loss of medium spiny neurons and astrogliosis. The first brain region to be substantially affected is the striatum, followed by degeneration of the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder, notably chorea. HD is caused by polyglutamine tract expansion in the huntingtin gene, resulting in the mutant huntingtin. Aggregates of mutant huntingtin form as inclusion bodies in neurons and may be directly toxic. Additionally, they may damage molecular motors and microtubules to interfere with normal axonal transport, leading to impaired transport of important cargoes such as BDNF.

In some embodiments, the method of treating a disease or condition related to protein aggregation comprises administering to a subject in need thereof a therapeutic effective amount of the pharmaceutical composition disclosed herein.

The therapeutically effective amount of the pharmaceutical composition provided herein will depend on various factors known in the art, such as for example type of disease to be treated, body weight, age, past medical history, present medications, state of health of the subject, immune condition and potential for cross-reaction, allergies, sensitivities and adverse side-effects, as well as the administration route and the type, the severity and development of the disease and the discretion of the attending physician or veterinarian. In certain embodiments, the pharmaceutical composition provided herein may be administered at a therapeutically effective dosage of about 0.001 mg/kg to about 100 mg/kg one or more times per day (e.g., about 0.001 mg/kg, about 0.3 mg/kg, about 0.5 mg/kg, about 1 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg one or more times per day). In certain embodiments, the pharmaceutical composition is administered at a dosage of about 50 mg/kg or less, and in certain embodiments the dosage is 20 mg/kg or less, 10 mg/kg or less, 3 mg/kg or less, 1 mg/kg or less, 0.3 mg/kg or less, 0.1 mg/kg or less, or 0.01 mg/kg or less, or 0.001 mg/kg or less. In certain embodiments, the administration dosage may change over the course of treatment. For example, in certain embodiments the initial administration dosage may be higher than the subsequent administration dosages. In certain embodiments, the administration dosage may vary over the course of treatment depending on the reaction of the subject.

Dosage regimens may be adjusted to provide the optimum desired response (e.g., a therapeutic response). In certain embodiments, the pharmaceutical composition provided herein is administered to the subject at one time or over a series of treatments. In certain embodiments, the pharmaceutical composition provided herein is administered to the subject by one or more separate administrations, or by continuous infusion depending on the type and severity of the disease.

The pharmaceutical composition provided herein may be administered by any route known in the art, such as for example parenteral (e.g., subcutaneous, intraperitoneal, intravenous, including intravenous infusion, intramuscular, intradermal or intrathecal injection) or non-parenteral (e.g., oral, intranasal, intraocular, sublingual, rectal, or topical) routes.

In some embodiments, the pharmaceutical composition is administered to the central nervous system. In some embodiments, the pharmaceutical composition is administered via spinal cord injection, intrathecal injection, intracerebroventricular injection, intracerebral injection, or intra-hippocampal injection. In some embodiments, the pharmaceutical composition provided herein is administered by intrathecal routes. As used herein, the terms "intrathecal administration," "intrathecal injection," "intrathecal delivery," or grammatic equivalents, refer to an injection into the spinal canal (intrathecal space surrounding the spinal cord). In some embodiments, "intrathecal administration" or "intrathecal delivery" according to the present disclosure refers to IT administration or delivery via the lumbar area or region (i.e., lumbar IT administration or delivery,) or cisterna *magna* delivery (i.e., injection via the space around and below the cerebellum via the opening between the skull and the top of the spine).

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

This example illustrates the effect of polypeptides RJK001 to RJK004 and control polypeptides RJK005 to RJK007 on dissolving the aggregation of FUS protein, TDP-43 protein, TIA1 protein and C9orf72 protein.

An in vitro system was provided in which the aggregates of the FUS protein (concentration 10 μM), TDP-43 protein (concentration 10 μM), TIA1 protein (concentration 30 μM) and C9orf72 protein (concentration 10 μM, 10% PEG) were formed. Under the condition of pH 7.5, 10 μM polypeptides RJK001 to RJK004 and control polypeptides RJK005 to RJK007 were respectively added to the systems. A confocal laser microscope was used to observe the effects of polypeptides RJK001 to RJK004 and RJK005 to RJK007 on the aggregation of FUS protein, TDP-43 protein, TIA1 protein and C9orf72 protein, and the results are shown in FIGS. 2-5.

As shown in FIG. 2, 10 μM polypeptides RJK001 to RJK004 and RJK005 to RJK007 were added respectively to seven parallel FUS protein solutions (pH 7.5, 10 μM FUS) that had aggregates. The effects of RJK001 to RJK004 and RJK005 to RJK007 on the aggregation of FUS protein were observed. The left image is the image just after adding the polypeptides. The middle image is the microscopic image when the polypeptides were added for 40 seconds. The right image is the microscopic image when the polypeptides were added for 80 seconds. It can be clearly observed from FIG. 2 that the FUS protein solution showed typical aggregation (phase separation droplets) when the peptides RJK001 to RJK004 were just added (0s). Forty seconds after the polypeptides RJK001 to RJK004 were added, the aggregation of FUS protein was significantly reduced (the phase-separated droplets were significantly reduced). Eighty seconds after the addition of polypeptides RJK001 to RJK004, the aggregation of FUS protein almost disappeared (almost no phase-separated droplets). Therefore, polypeptides RJK001 to RJK004 can significantly dissolve the aggregation of FUS protein. However, after adding polypeptides RJK005 to RJK007, the FUS protein solution still showed typical aggregation (phase separation droplets). Hence, the polypeptides RJK005 to RJK007 are not capable of effectively dissolving the FUS aggregates.

Figure 3:
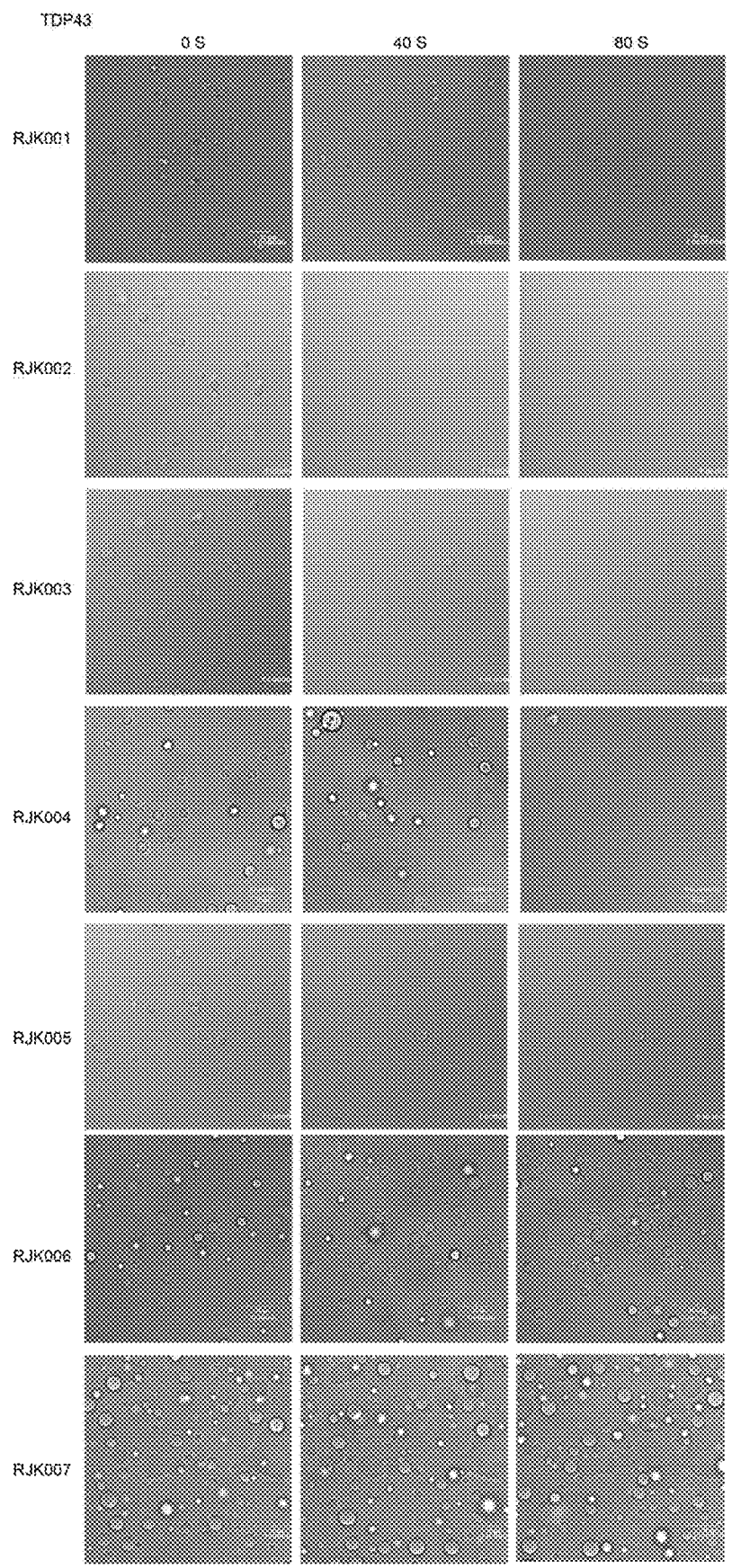
FIG. 3 shows that polypeptide RJK001~RJK004 dissolved TDP-43 protein aggregate in vitro. The prokaryotic expressed and purified TDP43 protein (pH7.5, 10 uM TDP-43) was induced to form phase separated droplets in vitro. Polypeptides RJK001~RJK007 (30 uM) were added dropwise to the TDP43 droplets. The observation was performed continuously through a confocal laser microscope. The left image is the microscopic image just after adding the polypeptides. The middle image is the microscopic image when the polypeptides were added for 40 seconds. The right image is the microscopic image when the polypeptides were added for 80 seconds.

As shown in FIG. 3, 10 μM polypeptides RJK001 to RJK004 and RJK005 to RJK007 were added respectively to seven parallel TDP-43 protein solutions (pH 7.5, 10 μM TDP-43) that had aggregates. The effects of RJK001 to RJK004 and RJK005 to RJK007 on the aggregation of TDP-43 protein was observed. The left image is the image just after adding the polypeptides. The middle image is the microscopic image when the polypeptides were added for 40 seconds. The right image is the microscopic image when the polypeptides were added for 80 seconds. It can be clearly observed from FIG. 3 that the TDP-43 protein solution showed typical aggregation (phase separation droplets) when the peptides RJK001 to RJK004 were just added (0s). Forty seconds after the polypeptides RJK001 to RJK004 were added, the aggregation of TDP43 protein was significantly reduced (the phase-separated droplets were significantly reduced). Eighty seconds after the addition of polypeptides RJK001 to RJK004, the aggregation of TDP43 protein almost disappeared (almost no phase-separated droplets). Therefore, polypeptides RJK001 to RJK004 can significantly dissolve the aggregation of TDP43 protein. However, after adding polypeptides RJK005 to RJK007, the TDP43 protein solution still showed typical aggregation (phase separation droplets). Hence, the polypeptides RJK005 to RJK007 are not capable of effectively dissolving the TDP43 aggregates.

Figure 4:
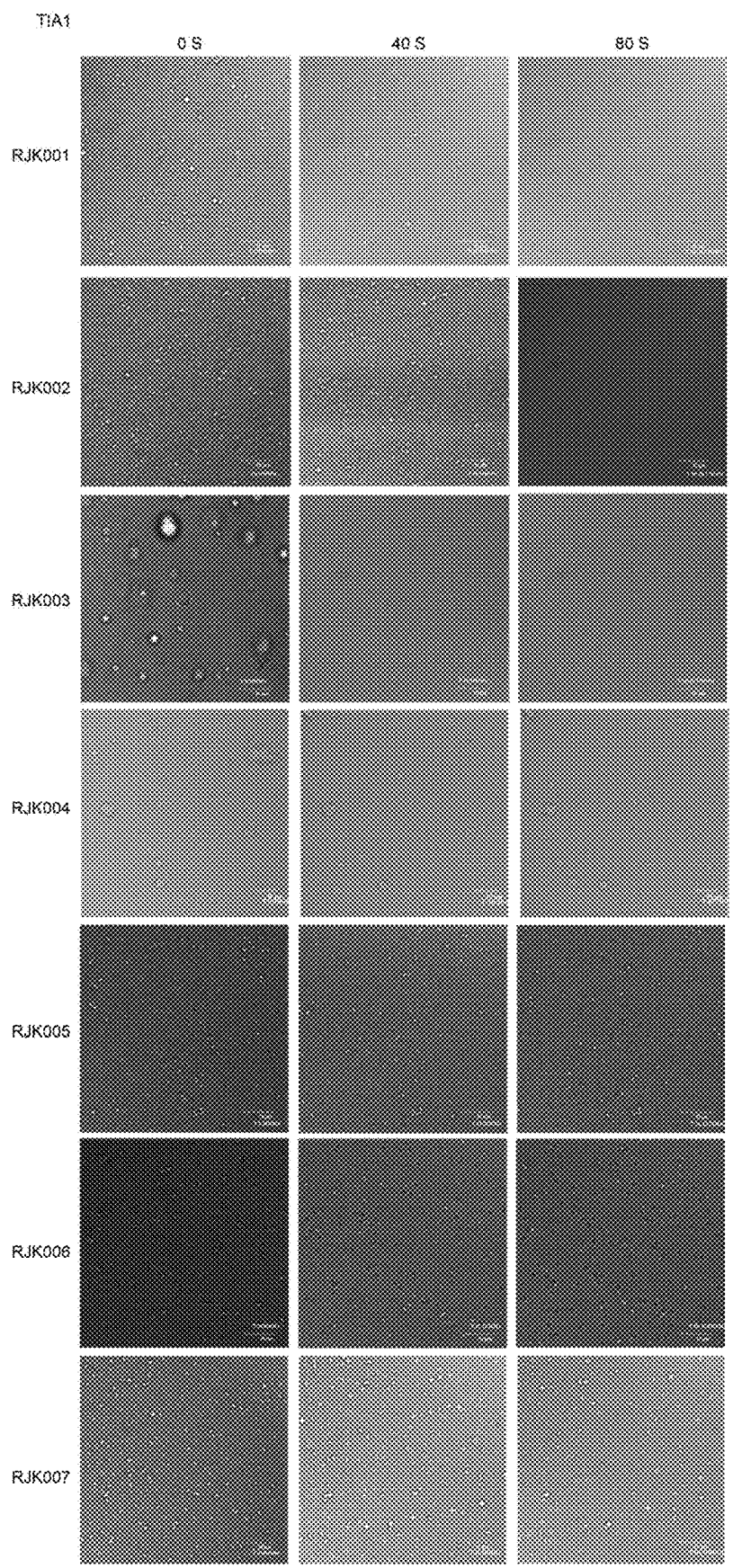
FIG. 4 shows that polypeptides RJK001~RJK004 dissolved TIA1 protein aggregates in vitro. Polypeptides RJK001~RJK007 (90 uM) were added dropwise to the TIA1 protein solution (pH7.5, 30 uM TIA1) having protein aggregates. The observation was performed continuously through a confocal laser microscope. The left image is the microscopic image just after adding the polypeptides. The middle image is the microscopic image when the polypeptides were added for 40 seconds. The right image is the microscopic image when the polypeptides were added for 80 seconds.

As shown in FIG. 4, 90 μM polypeptides RJK001 to RJK004 and RJK005 to RJK007 were added respectively to seven parallel TIA1 protein solutions (pH 7.5, 30 μM TIA1) that had aggregates. The effects of RJK001 to RJK004 and RJK005 to RJK007 on the aggregation of TIA1 protein was observed. The left image is the image just after adding the polypeptides. The middle image is the microscopic image when the polypeptides were added for 40 seconds. The right image is the microscopic image when the polypeptides were added for 80 seconds. It can be clearly observed from FIG. 4 that the TIA1 protein solution showed typical aggregation (phase separation droplets) when the peptides RJK001 to RJK004 were just added (0s). Forty seconds after the polypeptides RJK001 to RJK004 were added, the aggregation of TIA1 protein was significantly reduced (the phase-separated droplets were significantly reduced). Eighty seconds after the addition of polypeptides RJK001 to RJK004, the aggregation of TIA1 protein almost disappeared (almost no phase-separated droplets). Therefore, polypeptides RJK001 to RJK004 can significantly dissolve the aggregation of TIA1 protein. However, after adding polypeptides RJK005 to RJK007, the TIA1 protein solution still showed typical aggregation (phase separation droplets). Hence, the polypeptides RJK005 to RJK007 are not capable of effectively dissolving the TIA1 aggregates.

Figure 5:
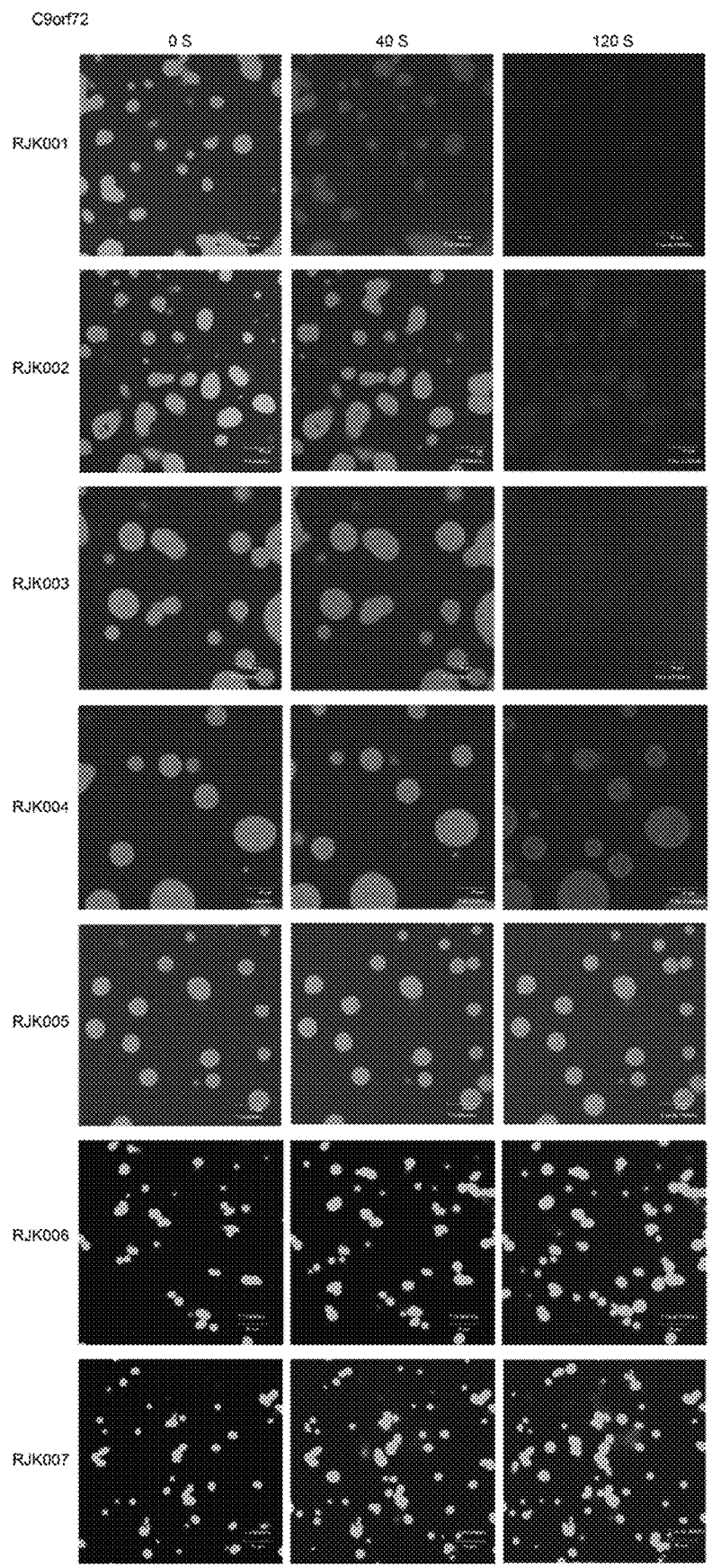
FIG. 5 shows that polypeptides RJK001~RJK004 dissolved GR50-GFP protein aggregates in vitro. Polypeptides RJK001~RJK007 (10 uM) were added dropwise to the GR50-GFP protein solution (translated from C9orf72 non-coding RNA, 10 uM, in 10% PEG) having protein aggregates. The observation was performed continuously through a confocal laser microscope. The left image is the microscopic image just after adding the polypeptides. The middle image is the microscopic image when the polypeptides were added for 40 seconds. The right image is the microscopic image when the polypeptides were added for 80 seconds.

As shown in FIG. 5, 90 μM polypeptides RJK001 to RJK004 and RJK005 to RJK007 were added respectively to seven parallel GR50-GFP (translated from non-coding gene C9orf72) protein solutions (pH 7.5, 10 μM) that had aggregates. The effects of RJK001 to RJK004 and RJK005 to RJK007 on the aggregation of GR50-GFP protein was observed. The left image is the image just after adding the polypeptides. The middle image is the microscopic image when the polypeptides were added for 40 seconds. The right image is the microscopic image when the polypeptides were added for 80 seconds. It can be clearly observed from FIG. 5 that the GR50-GFP protein solution showed typical aggregation (phase separation droplets) when the peptides RJK001 to RJK004 were just added (0s). Forty seconds after the polypeptides RJK001 to RJK004 were added, the aggregation of GR50-GFP protein was significantly reduced (the phase-separated droplets were significantly reduced). Eighty seconds after the addition of polypeptides RJK001 to RJK004, the aggregation of GR50-GFP protein almost disappeared (almost no phase-separated droplets). Therefore, polypeptides RJK001 to RJK004 can significantly dissolve the aggregation of TIA1 protein. However, after adding polypeptides RJK005 to RJK007, the GR50-GFP protein solution still showed typical aggregation (phase separation droplets). Hence, the polypeptides RJK005 to RJK007 are not capable of effectively dissolving the GR50-GFP aggregates.

Therefore, according to the above observation results, the polypeptides RJK001 to RJK004 have obvious dissolving effects on the in vitro aggregation of FUS protein, TDP-43 protein, TIA1 protein and C9orf72 protein, while the polypeptides RJK005 to RJK007, in which the E residues are mutated to Q, had no dissolving effect.

Example 2

This example illustrates the preparation of SH-SY5Y cell model.

An SH-SY5Y cell model that overexpresses FUS-GFP protein or TDP-43-mCherry protein was generated using the following steps:

Culture of SH-SY5Y Cells

SH-SY5Y cells were cultured in DMEM/F12 medium containing 10% fetal bovine serum in a 37° C., 5% carbon dioxide incubator. After the cell confluence reaches 80%, the culture medium was removed using a vacuum pump or pipette. The cells were washed once with PBS. Add trypsin-EDTA (0.05%) to the culture dish and incubate it in a 37° C. cell incubator for 1 min. Add twice the volume of culture medium to stop the digestion, and gently blow the cells to suspend the cells into a uniform cell suspension. Add the cell suspension to a 15 mL centrifuge tube and centrifuge at 1200 rpm for 3 minutes. Discard the supernatant and resuspend the cells in fresh complete medium. Re-add the cells to the culture dish and passage the cells at 1:6 to 1:4.

Transfection of SH-SY5Y Cells

To generate SH-SY5Y cell model transfected with FUS plasmids, dissolve 3 μg pCMV7.1-FUS-GFP plasmid and 6 ug liposome with 100 ul NaCl respectively. Add the liposome solution to DNA, mix well, and place at room temperature for 15-30 minutes. Add the above liquid to the cultured cells and mix well. Observe the cell culture after 24 hr.

The transfection operation of pCMV7.1-TDP43-mCherry plasmid is the same as above.

Example 3

This example illustrates the dissolving effect of RJK001 polypeptide on the aggregation of FUS protein, TIA1 protein and TDP-43 protein in cells.

Figure 6:
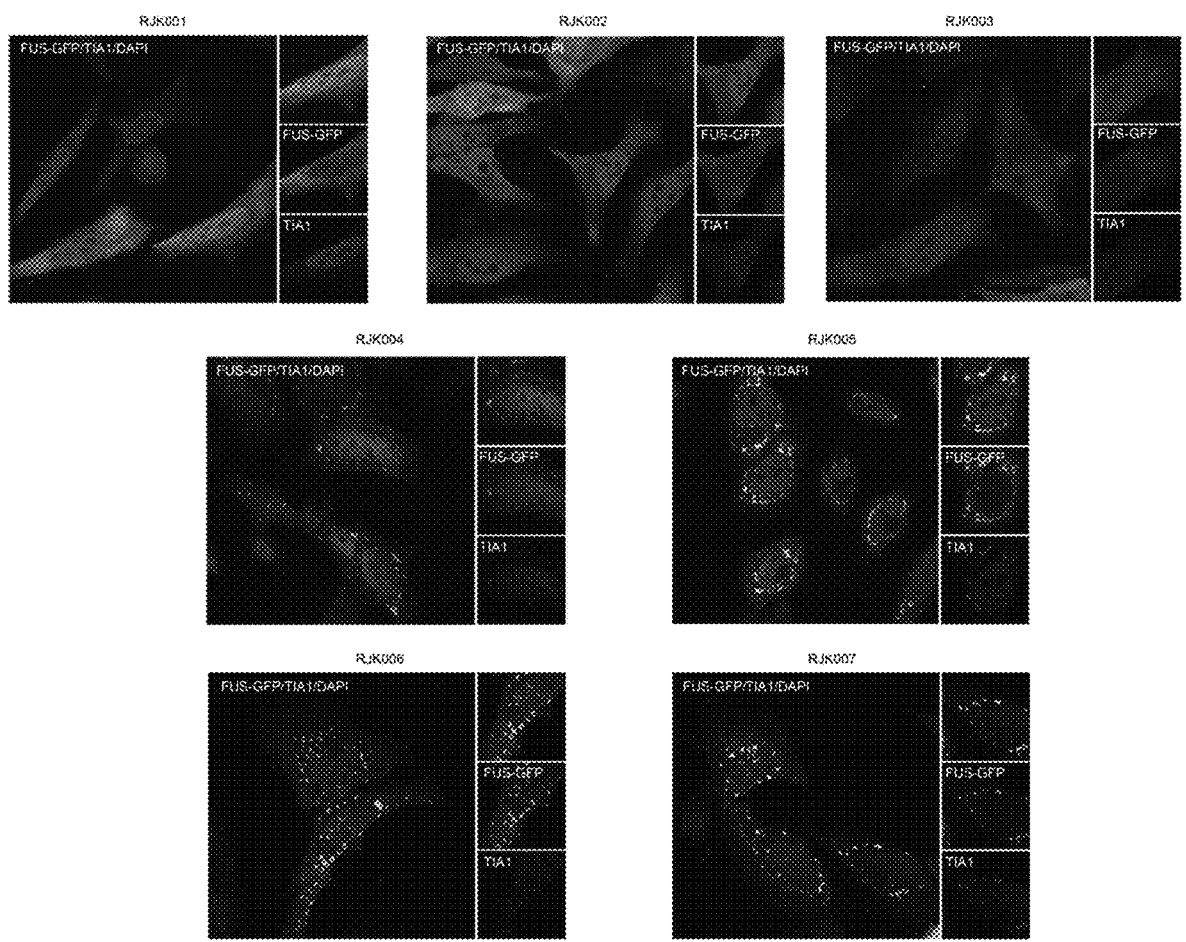
FIG. 6 shows the effect of RJK001~RJK007 polypeptides on the FUS protein aggregates in the SH-SY5Y cell mode. Polypeptides RJK001~RJK004 and control polypeptides RJK005~RJK007 were transfected into the SH-SY5Y cell model overexpressing FUS-mCherry after heat stimulation. The staining of G3BP1 represents the stress granule. RJK001~RJK004 polypeptides had a significant dissolution effect on the ALS pathogenic FUS aggregates, but the control polypeptides RJK005~RJK007 had no effect on the dissolution of the pathogenic FUS protein aggregates.

The SH-SY5Y cell model (initially cultured at 37° C.) transfected with the FUS plasmid according to Example 2 was placed in a 42° C. incubator for 1 hour for heat shock treatment to cause FUS protein aggregation. 1 µg RJK001 polypeptide-plasmid was added to the cell in the RJK001 experimental group. RJK005 to RJK007 polypeptide-plasmid were added to the call in the control group. After 1 hour, the cells were taken out, the membranes were fixed, and the SH-SY5Y-labeled stress granule protein G3BP1 was subjected to immunofluorescence staining according to the conventional immunofluorescence staining procedure. Laser confocal fluorescence microscope was used to observe the accumulation of overexpressed FUS in SH-SY5Y cells. As shown in FIG. 6, after 1 hour of heat shock treatment at 42° C., the number of phase-separated droplets of FUS protein and TIA1 protein in the RJK001 group was significantly less than that in the RJK005 to RJK007 control groups.

Figure 7:
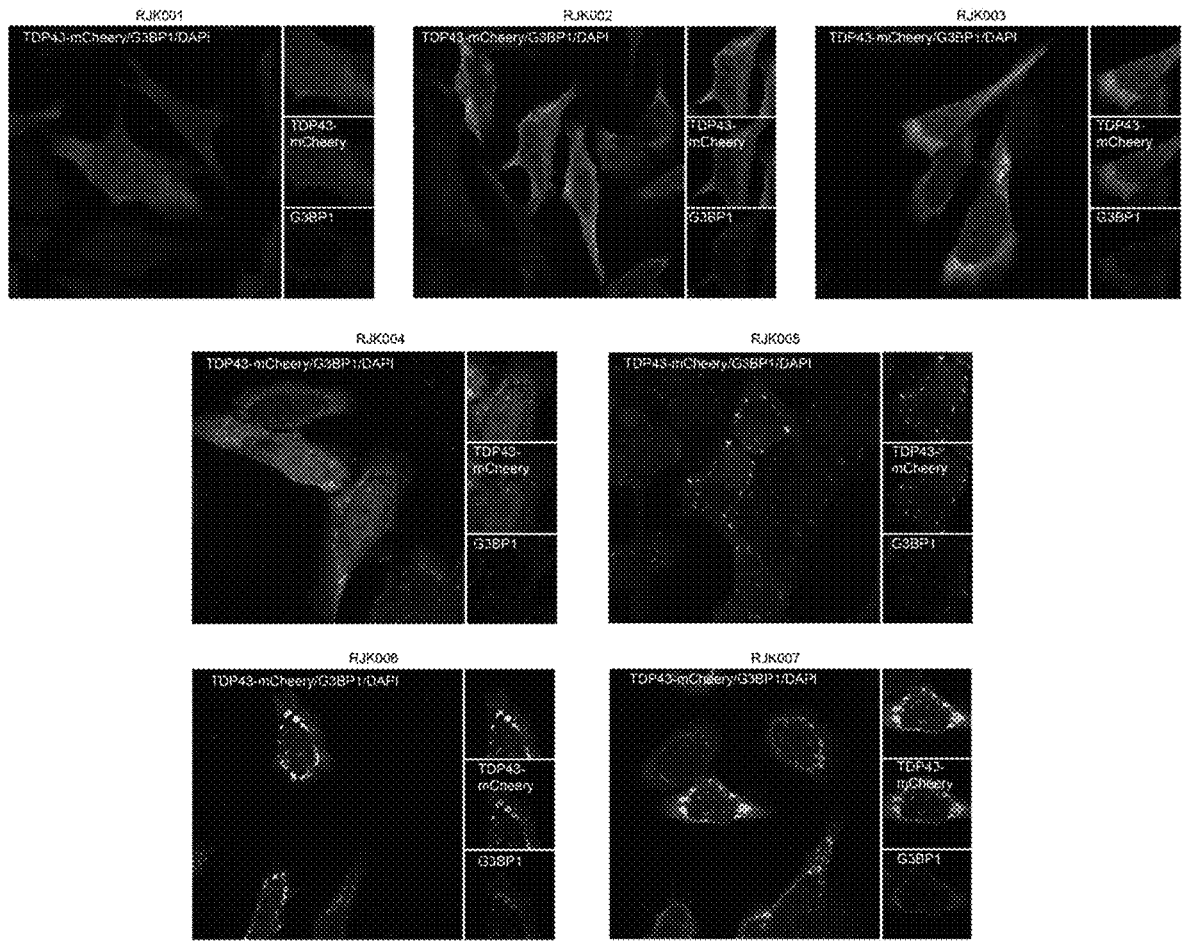
FIG. 7 shows the effect of RJK001~RJK007 polypeptides on the TDP-43 protein aggregates in the SH-SY5Y cell mode. Polypeptides RJK001~RJK004 and control polypeptides RJK005~RJK007 were transfected into the SH-SY5Y cell model overexpressing TDP-43-mCherry after heat stimulation. The staining of G3BP1 represents the stress granule. RJK001~RJK004 polypeptides had a significant dissolution effect on the ALS pathogenic TDP-43 aggregates, but the control polypeptides RJK005~RJK007 had no effect on the dissolution of the pathogenic TDP-43 protein aggregates.

The SH-SY5Y cell model (initially cultured at 37° C.) transfected with the TDP-43 plasmid prepared according to Example 2 was placed in a 42° C. incubator for 1 hour for heat shock treatment to cause the TDP43 protein to separate and aggregate. 1 µg RJK001 polypeptide-plasmid was added to the cell in the RJK001 experimental group. RJK005 to RJK007 polypeptide-plasmid were added to the call in the control group. After 1 hr, the cells were taken out, the membrane was fixed, and the SH-SY5Y labeled protein was immunofluorescently stained according to the conventional immunofluorescence staining procedure. Laser confocal fluorescence microscopy was used to observe the accumulation of TDP-43 and cell-endogenous G3BP1 in SH-SY5Y cells. As shown in FIG. 7, after 1 hour of heat shock treatment at 42° C., the number of phase-separated droplets of TDP-43 protein in the experimental group was significantly less than that in the control group.

Therefore, according to the above observation results, in the SH-SY5Y cell model, RJK001 polypeptide has a significant dissolving effect on the aggregation of FUS protein, TIA1 protein and TDP-43 protein.

Example 4

This example illustrates the preparation of ALS rat motor neuron model.

An ALS rat motor neuron model that can be used to overexpress FUS-GFP protein and SOD1 (G93A) protein was generated using the following steps.

Isolation and Cultivation of Rat Motor Neurons

After the E13.5 rat is anesthetized, open the abdominal cavity and take out the uterus to a 10 cm dish. Add HBSS, use scissors and tweezers to remove the embryos to a new dish. Separate the head and trunk of the embryo and move to anatomical spinal cord under a stereoscope. With the torso facing up, fix the hind limbs with a microscopic forceps. After finding the translucent spine, use another microscopic forceps to lift the skin forward and upward, and then open the connection on the side of the spine. Pick up the spine from the tail. Fix the head of the spine with the back side facing up and pick up the membrane. Turn the abdomen up, peel off the membrane, most of the DRG was removed. Remove the DRG attached to the spinal cord and move to a new 6 cm dish. Use micro tweezers to move the spinal cord to a 5 ml centrifuge tube, use tweezers to crush it to a size of 1 mm, add 1×Trypsin (diluted by HBSS), and place in a 37° C. incubator for 25-30 minutes. Use a 1 ml pipette tip to suck the tissue mass into the preheated 3 ml MN Medium and blow away the tissue mass. Pass the 40 um filer, transfer the cells to a 5 ml centrifuge tube, centrifuge at 400 g, 5 min to remove the supernatant. Resuspend the cells in 3 mlMN medium, take 10 ul and count. Plant $1.05 \times 10^6$ cells in a confocal small dish, 700 µl MN medium, adhere to the wall for 30 min to 1 hour, supplement 800 µl medium. Before seeding the cells, transfer the cells to 2 tubes for centrifugation. One tube of cells is resuspended with 800 µl electroporation solution, divided into 4 groups of plasmids, and then electrotransfected with Lonza 2b. After electrotransfection, transfer into 1 ml MN medium as soon as possible to make up the un-electrotransfeted. The cells are then transferred to a confocal small dish and placed in the incubator for 2 hours to adhere to the wall and then change the MN medium to remove the electroporation fluid as much as possible.

Transfection of Rat Motor Neurons

DIV 7 calcium transfer, calculate the bottom area of the dish and the amount of $CaCl_2$ and HBS. Replace the liquid in the medium with pre-warmed Neurobasal and collect the old medium for use. Add 500 ng plasmid to 12.5 ul 0.3M $CaCl_2$, quickly pipette 20-30 times and mix well. Add 12.5 ul HBS (pH 6.95-7.0) to the tube and store it in −20 aliquots. Pay attention to the pH, and quickly suck and mix. Add the liquid to each hole, turn the wrist to mix the culture medium in the neuron, put it back into the incubator for 60 minutes, small particles can be observed at the bottom of the dish. Bubble the Neurobasal medium with $CO_2$ 15 minutes in advance until it turns yellow and no longer changes color. Filter with 0.22 um filter for later use. Remove the culture medium on the neurons, add Neurobasal saturated with $CO_2$, put it back into the incubator for 15 minutes, and observe that the small particles in the dish disappear. Filter the old medium, add the new medium 1:1, and replace the Neurobasal in the dish with 1:1 medium. Put back into the incubator.

Example 5

This example illustrates the dissolving effect of RJK001 polypeptide on the ALS pathogenic protein FUS protein aggregates in rat motor neurons.

Figure 8:
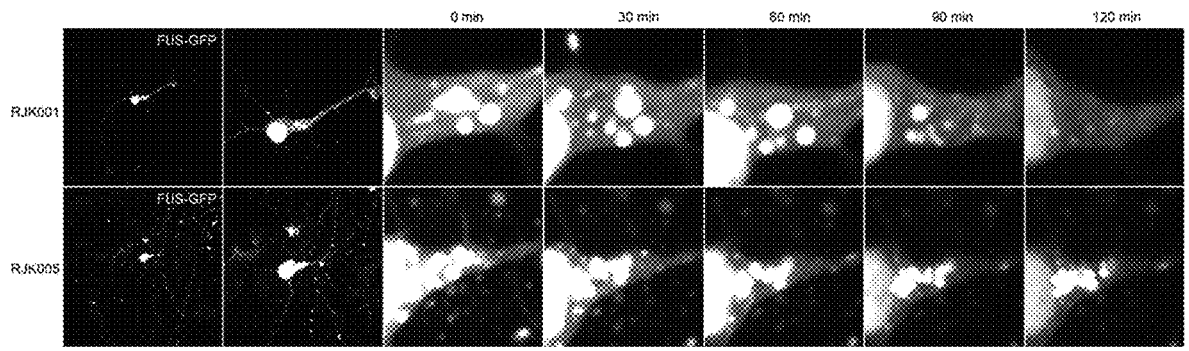
FIG. 8 shows the effect of polypeptide RJK001 and control polypeptide RJK005 on the ALS pathogenic FUS protein in primary cultured mouse motor neurons. RJK001 polypeptide enhanced the dissolution of FUS-GFP protein aggregates in mouse motor neurons while the control polypeptide had no effect on the dissolution of the pathogenic FUS protein aggregates. Real-time imaging technology using fluorescence microscope was used to observe the cell culture. The image on the left shows the motor neurons and protein aggregates on day 10 of in vitro culture. The left 2-3 images are the microscopic images when the polypeptides were just added (0 min); the middle images are the microscopic images at different time points (30 minutes, 60 minutes, 90 minutes) after the polypeptides were added, and the right image is the microscopic image at 120 minutes after adding the polypeptides.

A rat motor neuron model of ALS pathogenic FUS protein aggregates was prepared according to Example 4. RJK001 polypeptide (2004) was added to the model in the experiment group, and RJK005 polypeptide was added in the control group. The dissolution effect of the polypeptides on proteins aggregates in motor neurons was recorded with live images using laser confocal fluorescence microscope. FIG. 8 shows the microscope image of a single cell, where the upper panel is the experimental group (RJK001) and the lower panel is the control group (RJK005). In each panel of images, the image on the left is of motor neurons and protein aggregation on the 10th day of in vitro culture. The left 2-3 images are the microscopic images when the polypeptides are just added (0 min); the middle images are the microscopic images at different time points after the polypeptides were added (30 minutes, 60 minutes, 90 minutes), the right image is the microscopic image at 120 minutes after the polypeptides were added.

As shown in FIG. 8, the aggregation of ALS pathogenic proteins in the experimental group began to dissolve significantly at 90 minutes after adding the polypeptide RJK001, and essentially dissolved after 120 minutes, while the dissolution of the aggregates did not occur in the control group. Therefore, the RJK001 polypeptide has a significant dissolving effect on the FUS protein aggregates in the rat motor neuron model.

Example 6

This example illustrates the dissolving effect of RJK001 polypeptide on the ALS pathogenic protein SOD1 (G93A) protein aggregates in rat motor neurons.

Figure 9:
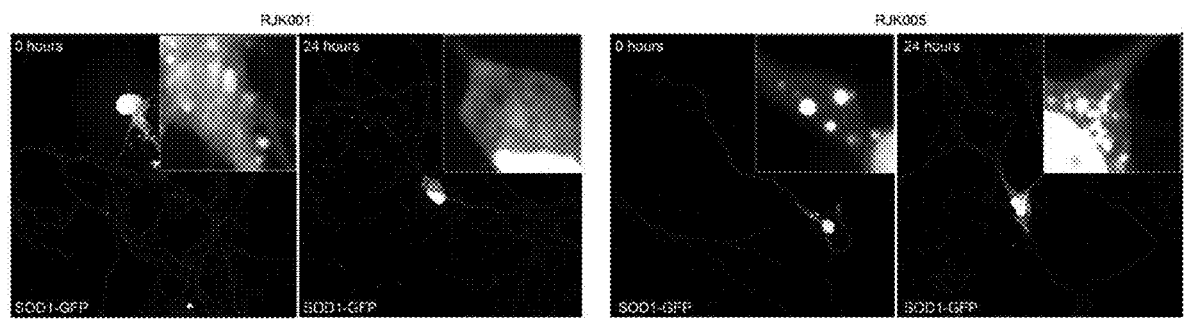
FIG. 9 shows the effect of polypeptide RJK001 and control polypeptide RJK005 on the ALS pathogenic SOD1 (G93A) protein in primary cultured mouse motor neurons. RJK001 polypeptide enhanced the dissolution of SOD1 (G93A)-GFP protein aggregates in mouse motor neurons while the control polypeptide had no effect on the dissolution of the protein aggregates. Real-time imaging technology using fluorescence microscope was used to observe the cell culture. The left panel is the polypeptide RJK001; the right panel is the control polypeptide RJK005. The left image in each panel shows the image of motor neurons and protein aggregates on day 10 of in vitro culture. The right image in each panel is the microscopic image at 24 hours after adding the polypeptides.

A rat motor neuron model of ALS pathogenic SOD1 (G93A) protein aggregates was prepared according to Example 4. RJK001 polypeptide (2004) was added to the model in the experiment group, and RJK005 polypeptide was added in the control group. The dissolution effect of the polypeptides on proteins aggregates in motor neurons was recorded with live images using laser confocal fluorescence microscope. FIG. 9 shows the microscope image of a single cell, where the left panel is the experimental group (RJK001) and the right panel is the control group (RJK005). In each panel of images, the image on the left is the image when the polypeptides are just added (0 hour); the right image is the microscopic image at 24 hours after the polypeptides were added.

As shown in FIG. 9, the aggregation of ALS pathogenic proteins in the experimental group dissolved significantly at 24 hours after adding the polypeptide RJK001, while the aggregates did not dissolve in the control group. Therefore, the RJK001 polypeptide has a significant dissolving effect on the ALS pathogenic SOD1 (G93A) protein aggregates in the rat motor neuron model.

Example 7

This example illustrates that intrathecal injection of virus carrying AAV2-9 serotype with RJK001 polypeptide to mouse ALS model dissolved ALS pathogenic protein SOD1 (G93A) protein aggregation in vivo.

hSOD1 (G93A) transgenic mice were purchased from Jackson Laboratory (Bar Harbor, ME, USA) and authenticated the genotype. The mice were randomly divided into 3 groups at 8 weeks of age wherein the first group received intrathecal injection of 10 ul normal saline after anesthesia; the second group (RJK001 experimental group) was intrathecally injected with AAV2-9 serotype RJK001; the third group (RJK005 control group) was intrathecal injected with AAV2-9 serotype RJK005.

Figure 10:
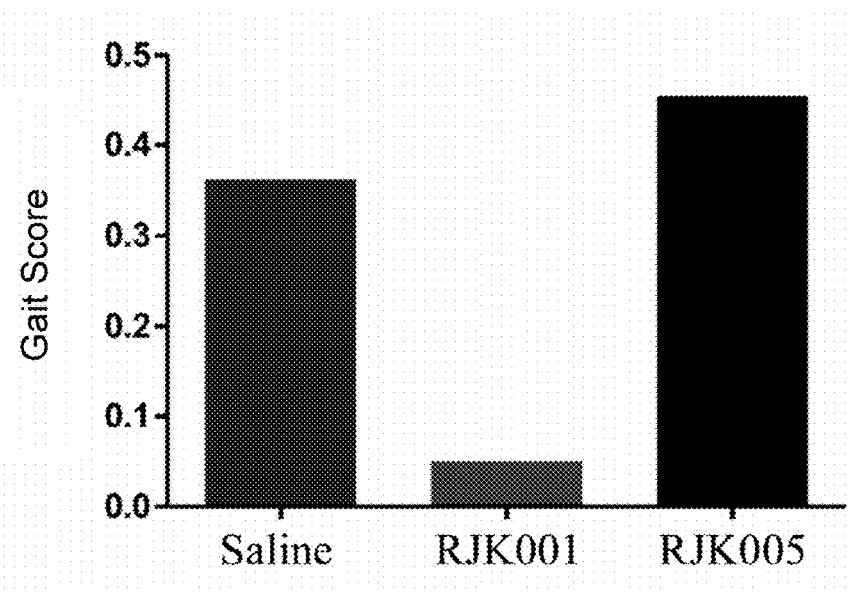
FIG. 10 shows that the introducing RJK001 polypeptide into SOD1(G93A) transgenic mice can effectively alleviate motor dysfunction in the animals. Two months old SOD1 (G93A) transgenic mice were given intrathecal injection of normal saline, AAV-RJK001 or AAV-RJK005. The results of the open field experiment on the motor function of mice are shown as solid bar: saline (control group), RJK001 (AAV-RJK001 virus injection), and RJK005 (AAV-RJK005 virus injection). The gait score of the open field experiment 6 weeks after the treatment is expressed by the time consumed per unit distance. The longer the time, the worse the exercise performance. Compared with the RJK005 and the control group, the exercise performance of the mice in the RJK001 experimental group was significantly improved.

Six weeks after the injection, an open field experiment was conducted on the mice, and the gait score was recorded as the time consumption per unit distance. The longer the time, the worse the moving ability. As shown in FIG. 10, compared with the normal saline and the RJK005 control group, the moving ability of the experimental group mice was significantly improved.

Example 8

This example illustrates the effect of polypeptides RJG001 to RJG003 on dissolving the aggregation of FUS protein.

An in vitro system was provided in which the aggregates of the FUS protein (concentration 10 µM) were formed. Under the condition of pH 7.5, 30 µM polypeptides RJG001 to RJG003 and control polypeptide RJK005 were respectively added to the systems. A confocal laser microscope was used to observe the effects of polypeptides RJG001 to RJG003 and RJK005 on the aggregation of FUS protein, and the results are shown in FIG. 11.

Figure 11:
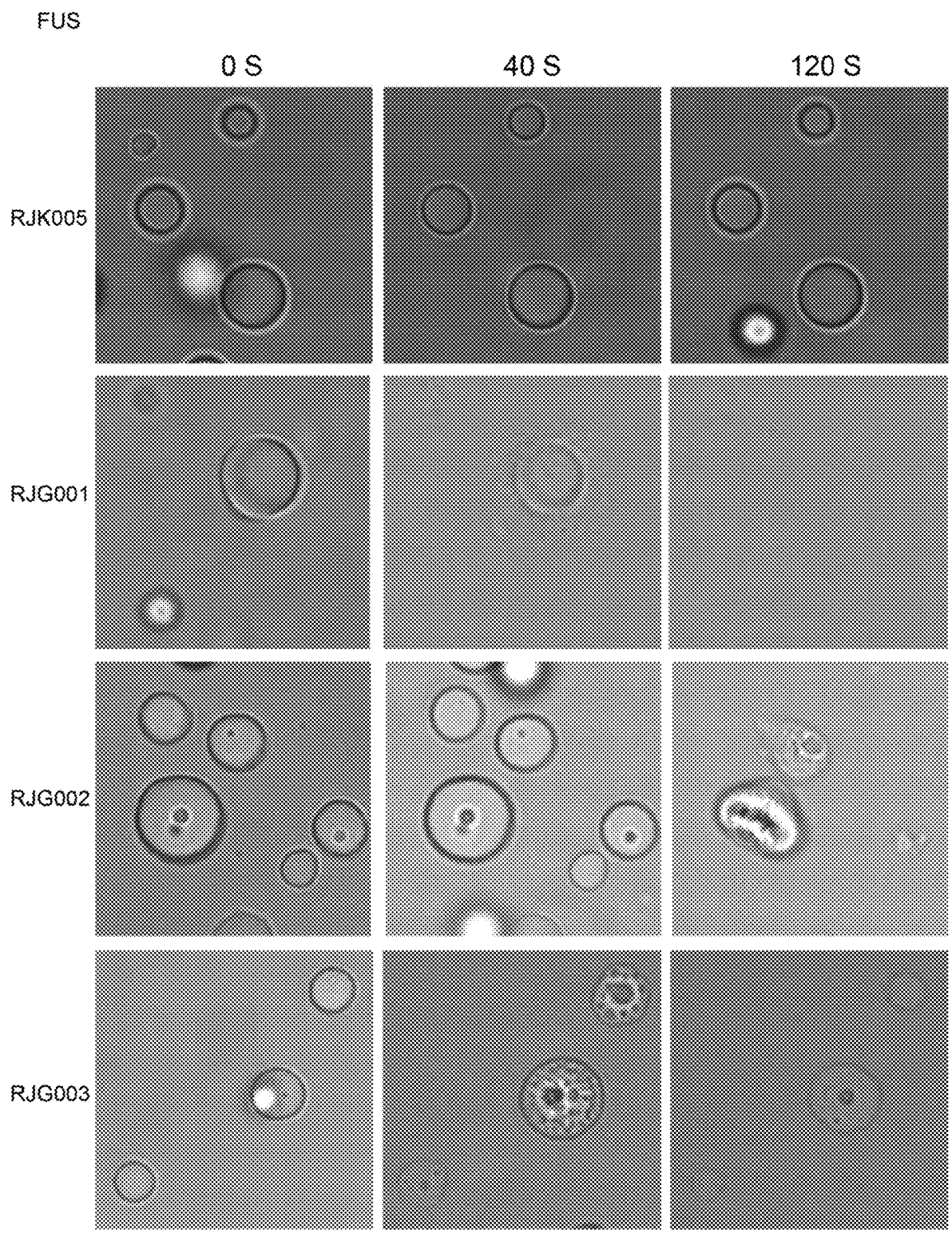
FIG. 11 shows that polypeptide RJG-001~RJG-003 dissolved FUS protein aggregates in vitro. The prokaryotic expressed and purified FUS protein (pH7.5, 10 uM FUS) was induced to form phase separated droplets in vitro. Polypeptides RJG-001~RJG003 and RJK005 (30 uM) were added dropwise to the FUS droplets. The observation was performed continuously through a confocal laser microscope. The left image is the microscopic image just after adding the polypeptides. The middle image is the microscopic image when the polypeptides were added for 40 seconds. The right image is the microscopic image when the polypeptides were added for 80 seconds.

As shown in FIG. 11, the FUS protein solution showed typical aggregation (phase separation droplets) when the polypeptides RJG001 to RJG003 were just added (0s). Forty seconds after the polypeptides were added, the aggregation of FUS protein was reduced (the phase-separated droplets were reduced). Eighty seconds after the addition of polypeptides RJG001 to RJG003, the aggregation of FUS protein significantly reduced. Therefore, polypeptides RJG001 to RJG003 can significantly dissolve the aggregation of FUS protein. However, after adding polypeptide RJK005, the FUS protein solution still showed typical aggregation (phase separation droplets). Hence, the polypeptides RJG001 to RJG003 are not capable of effectively dissolving the FUS aggregates.

Example 9

This example illustrates the dissolving effect of RJG001 to RJG003npolypeptides on the aggregation of FUS protein in cells.

The SH-SYSY cell model (initially cultured at 37° C.) transfected with the FUS plasmid according to Example 2 was placed in a 42° C. incubator for 1 hour for heat shock treatment to cause FUS protein aggregation. 1 µg RJG001, RJG002 or RJG003 polypeptide-plasmid was added to the cell in the experimental group. RJK005 polypeptide was added to the call in the control group. After 1 hour, the cells were taken out, the membranes were fixed, and the SH-SY5Y-labeled stress granule protein G3BP1 was subjected to immunofluorescence staining according to the conventional immunofluorescence staining procedure. Laser confocal fluorescence microscope was used to observe the accumulation of overexpressed FUS in SH-SY5Y cells.

As shown in FIG. 12, after 1 hour of heat shock treatment at 42° C., the number of phase-separated droplets of FUS protein in the experimental groups was significantly less than that in the RJK005 control groups. Therefore, RJG001 to RJG003 can significantly dissolve the aggregation of FUS protein in the SH-SY5Y cell model.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A polypeptide comprising a hydrophilic segment and a hydrophobic segment,
wherein the hydrophilic segment comprises a sequence selected from the group consisting of:
TEPQEESEEEVEEPEER (SEQ ID NO: 15),
TDPQDDSDDDVDDPDDR (SEQ ID NO: 16),
TKPQKKSKKKVKKPKKR (SEQ ID NO: 17),
TRPQRRSRRRVRRPRRR (SEQ ID NO: 18),
ELDEESEDEVEEEQEDR (SEQ ID NO: 19),
KEEVDEDRDVDE (SEQ ID NO: 20), and
EKSEQDLE (SEQ ID NO: 21), or a sequence having at least 90% identity thereto,
wherein the hydrophobic segment comprises a sequence selected from the group consisting of:
TFYDQTVSNDL (SEQ ID NO: 22),
ANSAYYDAHPVTNGI (SEQ ID NO: 23),
PPQTAAREATSIPGFPAEGAIPLPV (SEQ ID NO: 24), and
EGEVAEEPNSRP (SEQ ID NO: 25), or a sequence having at least 90% identity thereto,
wherein the hydrophilic segment is at the N-terminus and the hydrophobic segment is at the C-terminus,
wherein the polypeptide has a length of 20-60 amino acid residues, and
wherein the polypeptide is capable of dissolving a protein aggregate.

2. The polypeptide of claim 1, wherein the protein aggregate is fused in sarcoma (FUS) aggregate, TAR DNA-binding protein 43 (TDP43) aggregate, T-cell intracellular antigen-1 (TIA1) aggregate, chromosome 9 open reading frame 72 (C9orf72) aggregate or a combination thereof.

3. A method for dissolving a protein aggregate in a cell, the method comprising introducing to the cell the polypeptide of claim 1, wherein the protein aggregate is FUS aggregate, and the cell is motor neuron.

4. A pharmaceutical composition comprising (1) the polypeptide of claim 1, and (2) a pharmaceutically acceptable carrier.

5. A polynucleotide encoding a polypeptide comprising a hydrophilic segment and a hydrophobic segment, wherein the hydrophilic segment comprises a sequence selected from the group consisting of:
TEPQEESEEEVEEPEER (SEQ ID NO: 15),
TDPQDDSDDDVDDPDDR (SEQ ID NO: 16),
TKPQKKSKKKVKKPKKR (SEQ ID NO: 17),
TRPQRRSRRRVRRPRRR (SEQ ID NO: 18),
ELDEESEDEVEEEQEDR (SEQ ID NO: 19),
KEEVDEDRDVDE (SEQ ID NO: 20), and
EKSEQDLE (SEQ ID NO: 21), or a sequence having at least 90% identity thereto,
wherein the hydrophobic segment comprises a sequence selected from the group consisting of:

TFYDQTVSNDL (SEQ ID NO: 22),
ANSAYYDAHPVTNGI (SEQ ID NO: 23),
PPQTAAREATSIPGFPAEGAIPLPV (SEQ ID NO: 24), and
EGEVAEEPNSRP (SEQ ID NO: 25), or a sequence having at least 90% identity thereto,
wherein the hydrophilic segment is at the N-terminus and the hydrophobic segment is at the C-terminus,
wherein the polypeptide has a length of 20-60 amino acid residues, and
wherein the polypeptide is capable of dissolving a protein aggregate.

6. The polynucleotide of claim 5, which is a DNA or an RNA.

7. A vector comprising the polynucleotide of claim 5.

8. The vector of claim 7, which is a virus vector.

9. The vector of claim 8, which is an AAV vector.

10. A recombinant virus comprising the polynucleotide of claim 5.

11. A pharmaceutical composition comprising (1) the polynucleotide of claim 5 and (2) a pharmaceutically acceptable carrier.

12. A method for treating a neurodegeneration disease in a subject in need thereof, the method comprising administering to the subject a therapeutic effective amount of the pharmaceutical composition of claim 11, wherein the neurodegeneration disease is amyotrophic lateral sclerosis (ALS).

13. The method of claim 12, wherein the pharmaceutical composition is administered to the central nervous system.

14. The method of claim 13, wherein the pharmaceutical composition is administered via spinal cord injection, intrathecal injection, intracerebroventricular injection, intracerebral injection, or intra-hippocampal injection.

15. A polypeptide comprising a hydrophilic segment and a hydrophobic segment, wherein the polypeptide comprises a sequence selected from the group consisting of:
TEPQEESEEEVEEPEERQQTPE-VVPDDSGTFYDQTVSNDLE (SEQ ID NO:1),
TDPQDDSDDDVDDPDDRQQTPDVVPDDSGTFYDQTVSNDLD (SEQ ID NO:2),
TKPQKK-SKKKVKKPKKRQQTPKVVPDDSGTFYDQTVSNDLK (SEQ ID NO:3),
TRPQRRSRRRVRRPRRRQQT-PRVVPDDSGTFYDQTVSNDLR (SEQ ID NO:4),
ELDEESEDEVEEEQEDRQPSPEPVQENANSAYY-DAHPVTNGIE (SEQ ID NO: 8),
KEEVDEDRDVDESSPQD-SPPSKASPAQDGRPPQTAAREATSIPGFPAEG AIPLPV (SEQ ID NO: 9), and
EGEVAEEPNSRPQEKSEQDLE (SEQ ID NO: 10),
or a sequence having at least 90% identity thereto,
wherein the polypeptide is capable of dissolving a protein aggregate.

* * * * *

SEQUENCE LISTING

```
Sequence total quantity: 25
SEQ ID NO: 1          moltype = AA  length = 41
FEATURE               Location/Qualifiers
REGION                1..41
                      note = Synthetic
```

```
                        source              1..41
                                            mol_type = protein
                                            organism = synthetic construct
SEQUENCE: 1
TEPQEESEEE VEEPEERQQT PEVVPDDSGT FYDQTVSNDL E                              41

SEQ ID NO: 2            moltype = AA   length = 41
FEATURE                 Location/Qualifiers
REGION                  1..41
                        note = Synthetic
source                  1..41
                        mol_type = protein
                        organism = synthetic construct
SEQUENCE: 2
TDPQDDSDDD VDDPDDRQQT PDVVPDDSGT FYDQTVSNDL D                              41

SEQ ID NO: 3            moltype = AA   length = 41
FEATURE                 Location/Qualifiers
REGION                  1..41
                        note = Synthetic
source                  1..41
                        mol_type = protein
                        organism = synthetic construct
SEQUENCE: 3
TKPQKKSKKK VKKPKKRQQT PKVVPDDSGT FYDQTVSNDL K                              41

SEQ ID NO: 4            moltype = AA   length = 41
FEATURE                 Location/Qualifiers
REGION                  1..41
                        note = Synthetic
source                  1..41
                        mol_type = protein
                        organism = synthetic construct
SEQUENCE: 4
TRPQRRSRRR VRRPRRRQQT PRVVPDDSGT FYDQTVSNDL R                              41

SEQ ID NO: 5            moltype = AA   length = 41
FEATURE                 Location/Qualifiers
REGION                  1..41
                        note = Synthetic
source                  1..41
                        mol_type = protein
                        organism = synthetic construct
SEQUENCE: 5
TQPQQQSQQQ VQQPQQRQQT PQVVPDDSGT FYDQTVSNDL Q                              41

SEQ ID NO: 6            moltype = AA   length = 32
FEATURE                 Location/Qualifiers
REGION                  1..32
                        note = Synthetic
source                  1..32
                        mol_type = protein
                        organism = synthetic construct
SEQUENCE: 6
TEPQEESEEE VEEPEERQQT PEVVPDDSGT FY                                        32

SEQ ID NO: 7            moltype = AA   length = 27
FEATURE                 Location/Qualifiers
REGION                  1..27
                        note = Synthetic
source                  1..27
                        mol_type = protein
                        organism = synthetic construct
SEQUENCE: 7
TEPQEESEEE VEEPEERQQT PEVVPDD                                              27

SEQ ID NO: 8            moltype = AA   length = 43
FEATURE                 Location/Qualifiers
REGION                  1..43
                        note = Synthetic
source                  1..43
                        mol_type = protein
                        organism = synthetic construct
SEQUENCE: 8
ELDEESEDEV EEEQEDRQPS PEPVQENANS AYYDAHPVTN GIE                            43

SEQ ID NO: 9            moltype = AA   length = 55
FEATURE                 Location/Qualifiers
REGION                  1..55
```

```
                            note = Synthetic
source                      1..55
                            mol_type = protein
                            organism = synthetic construct
SEQUENCE: 9
KEEVDEDRDV DESSPQDSPP SKASPAQDGR PPQTAAREAT SIPGFPAEGA IPLPV         55

SEQ ID NO: 10               moltype = AA  length = 21
FEATURE                     Location/Qualifiers
REGION                      1..21
                            note = Synthetic
source                      1..21
                            mol_type = protein
                            organism = synthetic construct
SEQUENCE: 10
EGEVAEEPNS RPQEKSEQDL E                                              21

SEQ ID NO: 11               moltype = AA  length = 17
FEATURE                     Location/Qualifiers
REGION                      1..17
                            note = Synthetic
SITE                        2
                            note = Xaa - Xaa is D, E, K or R
SITE                        5
                            note = Xaa - Xaa is D, E, K or R
SITE                        6
                            note = Xaa - Xaa is D, E, K or R
SITE                        8
                            note = Xaa - Xaa is D, E, K or R
SITE                        9
                            note = Xaa - Xaa is D, E, K or R
SITE                        10
                            note = Xaa - Xaa is D, E, K or R
SITE                        12
                            note = Xaa - Xaa is D, E, K or R
SITE                        13
                            note = Xaa - Xaa is D, E, K or R
SITE                        15
                            note = Xaa - Xaa is D, E, K or R
SITE                        16
                            note = Xaa - Xaa is D, E, K or R
SITE                        17
                            note = X - X is D, E, K or R
source                      1..17
                            mol_type = protein
                            organism = synthetic construct
SEQUENCE: 11
TXPQXXSXXX VXXPXXX                                                   17

SEQ ID NO: 12               moltype = AA  length = 17
FEATURE                     Location/Qualifiers
REGION                      1..17
                            note = Synthetic
SITE                        1
                            note = Xaa - Xaa is D, E, K or R
SITE                        3
                            note = Xaa - Xaa is D, E, K or R
SITE                        4
                            note = Xaa - Xaa is D, E, K or R
SITE                        5
                            note = Xaa - Xaa is D, E, K or R
SITE                        7
                            note = Xaa - Xaa is D, E, K or R
SITE                        8
                            note = Xaa - Xaa is D, E, K or R
SITE                        9
                            note = Xaa - Xaa is D, E, K or R
SITE                        11
                            note = Xaa - Xaa is D, E, K or R
SITE                        12
                            note = Xaa - Xaa is D, E, K or R
SITE                        13
                            note = Xaa - Xaa is D, E, K or R
SITE                        15
                            note = X - X is D, E, K or R
SITE                        16
                            note = X - X is D, E, K or R
SITE                        17
                            note = X - X is D, E, K or R
```

```
source                   1..17
                         mol_type = protein
                         organism = synthetic construct
SEQUENCE: 12
XLXXXSXXXV XXXQXXX                                                    17

SEQ ID NO: 13            moltype =    length =
SEQUENCE: 13
000

SEQ ID NO: 14            moltype =    length =
SEQUENCE: 14
000

SEQ ID NO: 15            moltype = AA   length = 17
FEATURE                  Location/Qualifiers
REGION                   1..17
                         note = Synthetic
source                   1..17
                         mol_type = protein
                         organism = synthetic construct
SEQUENCE: 15
TEPQEESEEE VEEPEER                                                    17

SEQ ID NO: 16            moltype = AA   length = 17
FEATURE                  Location/Qualifiers
REGION                   1..17
                         note = Synthetic
source                   1..17
                         mol_type = protein
                         organism = synthetic construct
SEQUENCE: 16
TDPQDDSDDD VDDPDDR                                                    17

SEQ ID NO: 17            moltype = AA   length = 17
FEATURE                  Location/Qualifiers
REGION                   1..17
                         note = Synthetic
source                   1..17
                         mol_type = protein
                         organism = synthetic construct
SEQUENCE: 17
TKPQKKSKKK VKKPKKR                                                    17

SEQ ID NO: 18            moltype = AA   length = 17
FEATURE                  Location/Qualifiers
REGION                   1..17
                         note = Synthetic
source                   1..17
                         mol_type = protein
                         organism = synthetic construct
SEQUENCE: 18
TRPQRRSRRR VRRPRRR                                                    17

SEQ ID NO: 19            moltype = AA   length = 17
FEATURE                  Location/Qualifiers
REGION                   1..17
                         note = Synthetic
source                   1..17
                         mol_type = protein
                         organism = synthetic construct
SEQUENCE: 19
ELDEESEDEV EEEQEDR                                                    17

SEQ ID NO: 20            moltype = AA   length = 12
FEATURE                  Location/Qualifiers
REGION                   1..12
                         note = Synthetic
source                   1..12
                         mol_type = protein
                         organism = synthetic construct
SEQUENCE: 20
KEEVDEDRDV DE                                                         12

SEQ ID NO: 21            moltype = AA   length = 8
FEATURE                  Location/Qualifiers
REGION                   1..8
                         note = Synthetic
source                   1..8
```

```
SEQUENCE: 21
EKSEQDLE                                                                    8

SEQ ID NO: 22          moltype = AA  length = 11
FEATURE                Location/Qualifiers
REGION                 1..11
                       note = Synthetic
source                 1..11
                       mol_type = protein
                       organism = synthetic construct
SEQUENCE: 22
TFYDQTVSND L                                                                11

SEQ ID NO: 23          moltype = AA  length = 15
FEATURE                Location/Qualifiers
REGION                 1..15
                       note = Synthetic
source                 1..15
                       mol_type = protein
                       organism = synthetic construct
SEQUENCE: 23
ANSAYYDAHP VTNGI                                                            15

SEQ ID NO: 24          moltype = AA  length = 25
FEATURE                Location/Qualifiers
REGION                 1..25
                       note = Synthetic
source                 1..25
                       mol_type = protein
                       organism = synthetic construct
SEQUENCE: 24
PPQTAAREAT SIPGFPAEGA IPLPV                                                 25

SEQ ID NO: 25          moltype = AA  length = 12
FEATURE                Location/Qualifiers
REGION                 1..12
                       note = Synthetic
source                 1..12
                       mol_type = protein
                       organism = synthetic construct
SEQUENCE: 25
EGEVAEEPNS RP                                                               12
```